(12) United States Patent
Nicolelis et al.

(10) Patent No.: US 6,993,392 B2
(45) Date of Patent: Jan. 31, 2006

(54) MINIATURIZED HIGH-DENSITY MULTICHANNEL ELECTRODE ARRAY FOR LONG-TERM NEURONAL RECORDINGS

(75) Inventors: Miguel A. L. Nicolelis, Chapel Hill, NC (US); Gary C. Lehew, Durham, NC (US); David J. Krupa, Durham, NC (US)

(73) Assignee: Duke University, Durham, NC (US)

( * ) Notice: Subject to any disclaimer, the term of this patent is extended or adjusted under 35 U.S.C. 154(b) by 593 days.

(21) Appl. No.: 10/097,312

(22) Filed: Mar. 14, 2002

(65) Prior Publication Data

US 2003/0176905 A1 Sep. 18, 2003

(51) Int. Cl.
*A61N 1/08* (2006.01)
(52) U.S. Cl. ...................................... 607/45
(58) Field of Classification Search ............... 600/373, 600/378, 393, 544, 545; 607/45, 46, 116
See application file for complete search history.

(56) References Cited

U.S. PATENT DOCUMENTS

| | | | |
|---|---|---|---|
| 4,461,304 A | 7/1984 | Kuperstein | |
| 4,878,913 A | 11/1989 | Aebischer et al. | |
| 5,037,376 A | 8/1991 | Richmond et al. | |
| 5,215,088 A | 6/1993 | Normann et al. | |
| 5,325,865 A | 7/1994 | Beckman et al. | |
| 5,361,760 A | 11/1994 | Normann et al. | |
| 5,524,338 A * | 6/1996 | Martyniuk et al. | ............ 29/825 |
| 5,617,871 A | 4/1997 | Burrows | |
| 5,638,826 A | 6/1997 | Wolpaw et al. | |
| 5,687,291 A | 11/1997 | Smyth | |
| 5,692,517 A | 12/1997 | Junker | |
| 5,735,885 A | 4/1998 | Howard, III et al. | |
| 5,758,651 A | 6/1998 | Nygard et al. | |
| 5,810,725 A | 9/1998 | Sugihara et al. | |
| 5,843,142 A | 12/1998 | Sultan | |
| 5,855,801 A | 1/1999 | Lin et al. | |
| 5,873,840 A | 2/1999 | Neff | |
| 5,928,228 A | 7/1999 | Kordis et al. | |
| 5,938,688 A | 8/1999 | Schiff | |
| 5,938,689 A | 8/1999 | Fischell et al. | |
| 5,938,690 A | 8/1999 | Law et al. | |
| 6,001,065 A | 12/1999 | DeVito | |
| 6,006,124 A | 12/1999 | Fischell et al. | |
| 6,016,449 A | 1/2000 | Fischell et al. | |
| 6,024,700 A | 2/2000 | Nemirovski et al. | |
| 6,024,702 A | 2/2000 | Iversen | |
| 6,027,456 A | 2/2000 | Feler et al. | |
| 6,038,477 A | 3/2000 | Kayyali | |
| 6,061,593 A | 5/2000 | Fischell et al. | |
| 6,092,058 A | 7/2000 | Smyth | |
| 6,113,553 A | 9/2000 | Chubbuck | |
| 6,125,300 A | 9/2000 | Weijand et al. | |
| 6,128,538 A | 10/2000 | Fischell et al. | |

(Continued)

OTHER PUBLICATIONS

Craelius, William, "*The Bionic Man: Restoring Mobility,*" *Science*, 295:1018-1021 (Feb. 8, 2002).

(Continued)

*Primary Examiner*—Robert E. Pezzuto
*Assistant Examiner*—Frances P. Oropeza
(74) *Attorney, Agent, or Firm*—Jenkins, Wilson & Taylor, P.A.

(57) ABSTRACT

A high-density multichannel microwire electrode array is disclosed. The array can comprise a variable number of electrodes. A method of assembling the array is further disclosed. Additionally, a plurality of devices employing the array are disclosed, including an intelligent brain pacemaker and a closed loop brain machine interface.

11 Claims, 8 Drawing Sheets

U.S. PATENT DOCUMENTS

| | | | |
|---|---|---|---|
| 6,134,474 | A | 10/2000 | Fischell et al. |
| 6,154,678 | A | 11/2000 | Lauro |
| 6,161,045 | A | 12/2000 | Fischell et al. |
| 6,163,725 | A | 12/2000 | Peckham et al. |
| 6,169,981 | B1 | 1/2001 | Werbos |
| 6,171,239 | B1 | 1/2001 | Humphrey |
| 6,175,762 | B1 | 1/2001 | Kirkup et al. |
| 6,181,965 | B1 | 1/2001 | Loeb et al. |
| 6,185,455 | B1 | 2/2001 | Loeb et al. |
| 6,216,045 | B1 | 4/2001 | Black et al. |
| 6,240,315 | B1 | 5/2001 | Mo et al. |
| 6,254,536 | B1 | 7/2001 | DeVito |
| 6,280,394 | B1 | 8/2001 | Maloney et al. |
| 6,353,754 | B1 | 3/2002 | Fischell et al. |
| 6,354,299 | B1 | 3/2002 | Fischell et al. |
| 6,358,202 | B1 | 3/2002 | Arent |
| 6,360,122 | B1 | 3/2002 | Fischell et al. |
| 6,427,086 | B1 | 7/2002 | Fischell et al. |
| 6,430,443 | B1 | 8/2002 | Karell |
| 6,459,936 | B2 | 10/2002 | Fischell et al. |
| 6,466,822 | B1 | 10/2002 | Pless |
| 6,473,639 | B1 | 10/2002 | Fischell et al. |
| 6,480,743 | B1 * | 11/2002 | Kirkpatrick et al. .......... 607/45 |
| 2001/0023368 | A1 | 9/2001 | Black et al. |
| 2001/0027336 | A1 | 10/2001 | Gielen et al. |
| 2001/0029391 | A1 | 10/2001 | Gluckman et al. |
| 2001/0051819 | A1 | 12/2001 | Fischell et al. |
| 2001/0056290 | A1 | 12/2001 | Fischell et al. |
| 2002/0002390 | A1 | 1/2002 | Fischell et al. |
| 2002/0013612 | A1 | 1/2002 | Whitehurst |
| 2002/0016638 | A1 | 2/2002 | Mitra et al. |
| 2002/0099412 | A1 | 7/2002 | Fischell et al. |
| 2002/0169485 | A1 | 11/2002 | Pless et al. |

OTHER PUBLICATIONS

Kensall D. Wise et al., "An Integrated-Circuit Approach to Extraceullar Microelectrodes," IEEE Transactions on Biomedical Engineering, vol. BME-17, No. 3, Jul. 1970, pp 238-247.

Donald R. Humphrey et al., "Predicting Measures of Motor Performance from Multiple Cortical Spike Trains," Science, New Series, vol. 170, Issue 3959, Nov. 13, 1970, pp 758-762.

A. Bohg, "Ethylene Diamine-Pyrocatechol-Water Mixture Shows Etching Anomaly in Boron-Doped Silicon," Journal of the Electrochemical Society, vol. 118, No. 2, Feb. 1971, pp 401-402.

Donald R. Humphrey, "Relating Motor Cortex Spike Trains to Measures of Motor Performance," Department of Physiology, Emory University, Brain Research, No. 40, 1972, pp 7-18.

Arnold Starr et al., "An Evaluation of Photoengraved Microelectrodes for Extracellular Single-Unit Recording," IEEE Transactions on Biomedical Engineering, vol. BME-20, No. 4, Jul. 1973, pp 291-293.

Kensall D. Wise et al., "A Low-Capacitance Multielectrode Probe for Use in Extracellular Neurophysiology," IEEE Transactions on Biomedical Engineering, vol. BME-22, No. 3, May 1975, pp 212-219.

V. B. Mountcastle et al., "Posterior Parietal Association Cortex of the Monkey: Command Functions for Operations Within Extrapersonal Space," The Journal of Neurophysiology, vol. 38, No. 4, 1975, pp 871-908.

Edward M. Schmidt, "Single Neuron Recording From Motor Cortex as a Possible Source of Signals for Control of External Devices," Annals of Biomedical Engineering, vol. 8, 1980, pp 339-349.

Spencer L. BeMent, et al., "Solid-State Electrodes for Multichannel Multiplexed Intracortical Neuronal Recording," IEEE Transactions on Biomedical Engineering, vol. BME-33, No. 2, Feb. 1986, pp 230-241.

Apostolos P. Georgopoulos et al., "Neuronal Population Coding of Movement Direction," Science, vol. 233, Sep. 26, 1986, pp 1416-1419.

Kenneth L. Drake et al., "Performance of Planar Multisite Microprobes in Recording Extracellular Single-Unit Intracortical Activity," IEEE Transactions on Biomedical Engineering, vol. 35, No. 9, Sep. 1988, pp 719-732.

Patrick K. Campbell et al., "A chronic intracortical electrode array: Preliminary results," Journal of Biomed. Material Res.: Applied Biomaterials, vol. 23, No. 2, 1989, pp 245-259.

Andrew R. Mitz et al., "Learning-dependent Neuronal Activity in the Premotor Cortex: Activity during the Acquisition of Conditional Motor Associations," The Journal of Neuroscience, vol. 11, No. 6, Jun. 1991, pp 1855-1872.

Patrick K. Campbell et al., "A Silicon-Based, Three-Dimensional Neural Interface: Manufacturing Processes for an Intracortical Electrode Array," IEEE Transactions, 1991, pp 758-768.

A. C. Hoogerwerf et al., "A Three-Dimensional Neural Recording Array," IEEE Transactions, 1991, pp 120-123.

Gregory T. A. Kovacs et al., "Regeneration Microelectrode Array for Peripheral Nerve Recording and Stimulation," Transactions on Biomedical Engineering, vol. 39, No. 9, Sep. 1992, pp 893-902.

Kelly E. Jones et al., "A Glass/Silicon Composite Intracortical Electrode Array," Annals of Biomedical Engineering, vol. 20, 1992, pp 423-437.

Reinhard Eckhorn et al., "A new method for the insertion of multiple microprobes into neural and muscular tissue, including fiber electrodes, fine wires, needles and microsensors," Journal of Neuroscience Methods, vol. 49, 1993, pp 175-179.

Craig T. Nordhausen et al.,"Optimizing recording capabilities of the Utah Intracortical Electrode Array," Brain Research, vol. 637, Nos. 1/2, Feb. 21, 1994, pp 27-36.

Jamille F. Hetke et al., "Silicon Ribbon Cables for Chronically Implantable Microelectrode Arrays," IEEE Transactions on Biomedical Engineering, vol. 41, No. 4, Apr. 1994, pp 314-321.

Arnold C. Hoogerwerf et al., "A Three-Dimensional Microelectrode Array for Chronic Neural Recording," IEEE Transactions on Biomedical Engineering, vol. 41, No. 12, Dec. 1994, pp 1136-1146.

Camilo Toro et al., "8-12 Hz rhythmic oscillations in human motor cortex during two-dimensional arm movements: evidence for representation of kinematic parameters," Departments of Neurology, Neurosurgery, and Physiology, University of Minnesota; MINCEP Epilepsy Care, P.A.; The Minnesota Epilepsy Group of United and St. Paul Children's Hospital; and Human Motor Control Section, National Institute of Neurological Disorders and Stroke, National Institutes of Health, Electroencephalography and Clinical Neurophysiology, No. 93, 1994, pp 390-403.

Miguel A. L. Nicolelis et al., "Sensorimotor Encoding by Synchronous Neural Ensemble Activity at Multiple Levels of the Somatosensory System," Science, vol. 268, Jun. 2, 1995, pp 1353-1358.

Jerome N. Sanes et al., "Shared Neural Substrates Controlling Hand Movements in Human Motor Cortex," Science, vol. 268, Jun. 23, 1995, pp. 1775-1777.

D. M. Halliday et al., "A Framework for the Analysis of Mixed Time Series/Point Process Data-Theory and Application to the Study of Physiological Tremor, Single Motor Unit Discharges and Electromyograms," Progress in Biophysics Molecular Biology, vol. 64, Nos. 2/3, 1995, pp 237-278.

Qing Bai et al., "A High-Yield Process for Three-Dimensional Microelectrode Arrays," Solid-State Sensor and Actuator Workshop, Hilton Head, South Carolina, Jun. 2-6, 1996, pp 262-265.

Changhyun Kim et al., "A 64-Site Multishank CMOS Low-Profile Neural Stimulating Probe," IEEE Journal of Solid-State Circuits, vol. 31, No. 9, Sep. 1996, pp 1230-1238.

Gwo-Ching Chang et al., "Real-time implementation of electromyogram pattern recognition as a control command of man-machine interface," Medical Engineering Phys., vol. 18, No. 7, 1996, pp 529-537.

P. Nisbet, "Integrating assistive technologies: current practices and future possibilities," Med. Eng. Phys., vol. 18, No. 3, 1996, pp 193-202.

TR Scott et al., "The Monitoring Tendon Tension with an Implantable Intratendon Probe and its Use in the Control of Neuroprostheses," IEEE Transactions on Rehabilitation Engineering, vol. 5, No. 2, Jun. 1997, pp 233-235.

Barbara M. Faggin et al., "Immediate and simultaneous sensory reorganization at cortical and subcortical levels of the somatosensory system," Proc. Natl. Acad. Science USA, vol. 94, Aug. 1997, pp 9428-9433.

Robert M. Bradley et al., "Long term chronic recordings from peripheral sensory fibers using a sleve electrode array," Journal of Neuroscience Methods, vol. 73, 1997, pp 177-186.

David K. Warland et al., "Decoding Visual Information From a Population of Retinal Ganglion Cells," The American Physiological Society, 1997, pp 2336-2350.

Steven P. Wise et al., "Premotor and Parietal Cortex: Cortiococortical Connectivity and Combinatorial Computations," Annual Review of Neuroscience, vol. 20, 1997, pp 25-42.

P. R. Kennedy et al., "Restoration of neural output from a paralyzed patient by a direct brain connection," NeuroReport, vol. 9, No. 8, Jun. 1998 pp.1707-1711.

Paolo Dario et al., "Neural Interfaces for Regenerated Nerve Stimulation and Recording," IEEE Transactions on Rehabilitation Engineering, vol. 6, No. 4, Dec. 1998, pp 353-363.

Nicholas G. Hatsopoulos et al., "Information about movement direction obtained from synchronous activity of motor cortical neurons," Proc. Natl. Acad. Sci. USA, vol. 95, Dec. 1998, pp 15706-15711.

John P. Donoghue et al., "Neural Discharge and Local Field Potential Oscillations in Primate Motor Cortex During Voluntary Movements," The American Physiological Society, 1998, pp 159-173.

Gregor Rainer et al., "Prospective Coding for Objects in Primate Prefrontal Cortex," The Journal of Neuroscience, vol. 19, No. 13, Jul. 1, 1999, pp 5493-5505.

John K. Chapin et al., "Real-time control of a robot arm using simultaneously recorded neurons in the motor cortex," Department of Neurobiology and Anatomy, MCP Hahnemann School of Medicine; and Department of Neurobiology, Duke University Medical Center, Nature Neuroscience vol. 2, No. 7, Jul. 1999, pp 664-670.

E. M. Maynard et al., "Neuronal Interactions Improve Cortical Population Coding of Movement Direction," The Journal of Neuroscience, vol. 19, No. 18, Sep. 15, 1999, pp. 8083-8093.

F. Gandolfo et al., "Cortical correlates of learning in monkeys adapting to a new dynamical environment," PNAS, vol. 97, No. 5, Feb. 29, 2000, pp 2259-2263.

J. F. Marsden et al., Organization of Cortical Activities Related to Movement in Humans, The Journal of Neuroscience, vol. 20, No. 6, Mar. 15, 2000, pp 2037-2314.

D. Gareth Evans et al., "Controlling Mouse Pointer Position Using an Infrared Head-Operated Joystick," IEEE Transactions on Rehabilitation Engineering, vol. 8, No. 1, Mar. 2000, pp 107-117.

Qing Bai et al., "A High-Yield Microassembly Structure For Three-Dimensional Microelectrode Arrays," IEEE Transactions on Biomedical Engineering, vol. 47, No. 3, Mar. 2000, pp 281-289.

Jonathan R. Wolpaw et al., "Brain-Computer Interface Technology: A Review of the First International Meeting," IEEE Transactions on Rehabilitation Engineering, vol. 8, No. 2, Jun. 2000, pp 164-173.

Simon P. Levine et al., "A Direct Brain Interface Based on Event-Related Potentials," IEEE Transactions on Rehabilitation Engineering, vol. 8, No. 2, Jun. 2000, pp 180-185.

Johan Wessberg et al., "Real-time prediction of hand trajectory by ensembles of cortical neurons in primates," Nature, vol. 408, Nov. 16, 2000, pp 361-365.

Jerome N. Sanes et al., "Plasticity and Primary Motor Cortex," Annual Reviews, Neuroscience, Brown University Library, vol. 23, 2000, pp 393-415.

Jonathan C. Jarvis et al., "The application and technology of implantable neuromuscular stimulators: an introduction and overview," Medical Engineering & Physics, No. 23, Jan. 11, 2001, pp 3-7.

Miguel A. L. Nicolelis, "Real-time direct interfaces between the brain and electronic and mechanical devices could one day be used to restore sensory and motor functions lost through injury or disease. Hybrid brain-machine interfaces also have the potential to enhance our perceptual, motor and cognitive capabilities by revolutionizing the way we use computers and interact with remote environments," Nature, vol. 409, Jan. 18, 2001, pp 403-407.

Gerald E. Loeb et al., BION™ system for distributed neural prosthetic interfaces, Medical Engineering & Physics, vol. 23, Jan. 26, 2001, pp 9-18.

Patrick J. Rousche et al., "Flexible Polymide-Based Intracortical Electrode Arrays with Bioactive Capability," IEEE Transactions on Biomedical Engineering; vol. 48, No. 3, Mar. 2001, pp 361-371.

Qing Bai et al., "Single-Unit Neural Recording with Active Microelectrode Arrays," IEEE Transactions on Biomedical Engineering, vol. 48, No. 8, Aug. 2001, pp 911-920.

David L. Zealear et al., The Biocompatibility, Integrity, and Positional Stability of an Injectable Microstimulator for Reanimation of the Paralyzed Larynx, IEEE Transactions on Biomedical Engineering, vol. 48, No. 8, Aug. 2001, pp 890-897.

Dawn M. Taylor et al., Using Virtual Reality to Test the Feasibility of Controlling an Upper Limb Fes System Directly from Multiunit Activity in the Motor Cortex, Arizona State University; and The Neurosciences Institute, Summer 2001, pp 1-3.

Shay Shoham, "Advances Towards an Implantable Motor Cortical Interface," The University of Utah, Dec. 2001, pp 1-157.

John K. Chapin et al., "Neural Prostheses for Restoration of Sensory and Motor Function," CRC Press, LLC, 2001, Chapters 6, 8 and 9, pp 179-219, pp 235-261, pp 263-283.

Andrew B. Schwartz et al., "Extraction algorithms for cortical control of arm prosthetics," The Neuroscience Institute; and Department of Bioengineering, Arizona State University, 2001, pp 701-707.

István Ulbert et al., "Multiple microelectrode-recording system for human intracortical applications," Journal of Neuroscience Methods, vol. 106, 2001, pp 69-79.

Mijail D. Serruya et al., "Intstant Neural Control of a Movement Signal," Nature, vol. 416, Mar. 14, 2002, pp 141-142.

Dawn M. Taylor et al., "Direct Cortical Control of 3D Neuroprosthetic Devices," Science, vol. 296, Jun. 7, 2002, pp 1829-1832.

John P. Donoghue, "Connecting cortex to machines: recent advances in brain interfaces," Nature Neuroscience Supplement, vol. 5, Nov. 2002, pp 1085-1088.

Y. Gao, et al., "Probabilistic Inference of Hand Motion from Neural Activity in Motor Cortex," in Advances in Neural Information Processing Systems 14, The MIT Press, 2002, pp 1-8.

Mijail Serruya et al., "Robustness of neuroprosthetic decoding algorithms," Biological Cybernetics, 2003, pp 1-10.

* cited by examiner

MINIATURIZED HIGH-DENSITY MULTICHANNEL ELECTRODE ARRAY FOR LONG-TERM NEURONAL RECORDINGS

GRANT STATEMENT

This work was supported by DARPA grant N00014-98-0676. Thus, the U.S. Government has certain rights in the invention.

TECHNICAL FIELD

The present invention relates generally to an apparatus for acquiring neural signals and more particularly to an apparatus for acquiring neural signals from a large number of single neurons. The apparatus of the present invention is adapted for chronic implantation in the brain of subject and facilitates simultaneous acquisition of an unlimited number of neural signals.

ABBREVIATIONS

PCB printed circuit board
FPC flexible printed circuit board

BACKGROUND ART

Over the past ten years, there has been an explosive growth in the use of multi-channel neuronal recordings, for both basic neurobiology research as well as clinical applications (see, e.g., Chicurel, (2001) *Nature*, 412: 266–8; Nicolelis et al., (1997) *Neuron*, 18: 529–37; and Nicolelis, (ed.), *Methods for Neural Ensemble Recordings*, CRC Press, Boca Raton, 1998). However, during this time, progress in these fields has been limited by the design of the electrodes and electrode arrays presently available for clinical and research applications. In particular, the relatively large size and low electrode density of the presently available electrode array designs has limited the density of implanted electrodes to about 32 channels (or electrodes) per square centimeter. In comparison, because of the extremely high-density of neurons in the human (and other mammalian) brain, many researchers and clinicians cite a density of about 100 more electrodes per square millimeter as a theoretically ideal density of implanted electrodes. Therefore any improvement in electrode density would greatly facilitate work in these fields.

Prior art brain research instrumentation includes movable single channel or single electrode mechanisms that are limited to recording from a single location in the brain. Early research tended to be concentrated in sensory portions of the brain such as the visual cortex. For example, the research would seek to identify what particular stimulus in the subject's visual field would cause an individual neuron in the visual cortex to fire. The prior art single electrode mechanisms were capable of being moved to different locations in the brain but were only capable of recording from a single neuron or a small neuron cluster at a time.

The prior art also includes apparatuses with multiple electrodes whose position in space is fixed relative to the other electrodes. These prior art electrodes are capable of recording timing or firing patterns of multiple neurons or multiple small clusters of neurons. The importance of being able to record timing patterns is helpful to understanding higher order functions of the brain. However, the multichannel or multi-electrode prior art devices could only be employed in restrained subjects and were not capable of being moved within the brain.

Thus, neurology research and the development of clinical applications were limited by the number of electrodes and research was confined to only those patterns that occurred between the individual neurons or small neuron clusters that happen to be near the tips of the recording electrodes. Another disadvantage of the fixed array of electrodes is that the research is inherently limited to those brain functions performed by a non-moving subject.

Yet another limitation of prior art apparatuses is that they are unsuited to long-term implantation. In order to accurately study neural processes and to treat neural maladies, it is important to be able to acquire significant amounts of data over a long period of time. This is not possible using prior art apparatuses that cannot be implanted for long periods of time in the neural tissue of a subject.

Early efforts to implant electrodes in the brain tissue of a subject have met with some success, but still encounter many problems. In many prior art devices and methods, a wire, or wires, is implanted in the cortex, the wire is immobilized on the skull in some manner, and is connected to an amplification and recording device(s).

These prior art methods and devices are deficient because movement of the electrode within the skull can disrupt signal transmission or cause signal artifacts. Excessive rigidity of the electrode can cause, in addition to signal disruption, irritation and damage to the cortex. Additionally, there is the possibility of a local tissue reaction to the presence of a foreign body or scar tissue formation over time, which can decrease the usefulness of the electrode and the signal transmitted. Infection due to electrode wires can cause deleterious effects. Current implant electrodes have been used to record signals over a period of days or weeks, and in few instances, for several months. An electrode array is needed, therefore, that can transmit signals accurately over a longer period, since repeated operations on a subject to repair or replace an electrode are clearly undesirable. Additionally, freedom of movement is also often restricted by the bulky electrode arrays used by present techniques. Thus, it is desirable to have access to small electrode arrays that do not limit movement.

Further, it is desirable to simultaneously record data from large numbers of single neurons in comparatively small areas of a subject's brain. This can greatly enhance the quality and quantity of data recorded from a subject and can offer insight into neural processes and afflictions. However, to meet this desire, an apparatus preferably provides a high-density of implantable electrodes. By increasing the density of electrodes, a greater volume of data can be acquired, and thus a deeper understanding of neural processes can be obtained. Prior art apparatuses, however, are unsuited to this goal, due to their limited electrode density.

Yet another significant advantage in recording data from a large number of single neurons is that a wealth of basic neurophysiological data would become available, data that is not accessible through prior art electrode arrays. Questions regarding the functional organization of adjacent neurons, their relative activities during sensory perception, and their relative coordinated activities during motor output could be determined. Relative activity during conditioning and during learning of new tasks could be studied. Furthermore, implanting electrodes over different cortical areas could demonstrate functional interactions in a manner unavailable by any other means.

Summarily, prior art apparatuses do not disclose a high-density multichannel electrode array for long-term intracranial neuronal recordings. A high-density electrode array would be a great asset to researchers in the field of neurobiology and to researchers in related fields. The problem, then, is to develop a high-density multi-channel electrode array that can improve the density of implanted electrodes by a significant degree. The present invention solves this and other problems.

DISCLOSURE OF THE INVENTION

A multichannel microwire electrode array for acquiring neural signals from large numbers of single neurons is disclosed. In a preferred embodiment, the array comprises: (a) one or more microwire electrodes; (b) one or more printed circuit boards in electrical connection with the one or more microwire electrodes, the one or more printed circuit boards comprising: (i) one or more conductive traces spaced apart about 0.015 inches (center to center) or less; and (ii) one or more conductive pads in electrical connection with the one or more conductive traces; and (c) one or more connectors in electrical connection with the one or more conductive pads and having contacts spaced apart about 0.030 inches or less.

A method of assembling a multichannel microwire electrode array for acquiring neural signals from large numbers of single neurons is also disclosed. In a preferred embodiment, the method comprises: (a) associating one or more microwire electrodes with a printed circuit board comprising conductive traces spaced about 0.015 inches (center to center) or less and conductive pads in electrical connection with the conductive traces to form a PCB-electrode assembly; (b) applying a conductive paint to the PCB-electrode assembly to form a coated PCB-electrode assembly; and (c) associating the coated PCB-electrode assembly with at least one connector via the conductive pads, the connector comprising: (i) a contact adapted to electrically connect with each of the conductive pads; and (ii) a ground contact in order to form a multichannel microwire electrode array for acquiring neural signals from large numbers of single neurons.

Additionally, a multichannel microwire electrode array kit is disclosed. In a preferred embodiment, the kit comprises: (a) one or more microwire electrodes; (b) one or more printed circuit boards comprising: (i) one or more conductive traces spaced apart about 0.015 inches (center to center) or less; and (ii) one or more conductive pads in electrical connection with the one or more conductive traces; and (c) one or more connectors having contacts spaced apart about 0.030 inches (center to center) or less.

Further, a real time closed loop brain-machine interface is disclosed. In a preferred embodiment, the interface comprises: (a) a multichannel microwire electrode array for acquiring neural signals from large numbers of single neurons comprising: (i) one or more microwire electrodes; (ii) one or more printed circuit boards in electrical connection with the one or more microwire electrodes comprising: (1) one or more conductive traces spaced apart about 0.015 inches (center to center) or less; and (2) one or more conductive pads in electrical connection with the one or more conductive traces; and (iii) one or more connectors in communication with the one or more conductive pads and having contacts spaced apart about 0.030 inches (center to center) or less; (b) a signal processing mechanism adapted to communicate with the multichannel microwire electrode array and adapted to form extracted motor commands from the extracellular electrical signals; and (c) an actuator adapted to communicate with the signal processing mechanism and to respond to the extracted motor commands by effecting a movement, and to provide sensory feedback to the subject.

Also disclosed is a real time closed loop brain-machine interface for restoring voluntary motor control and sensory feedback to a subject that has lost a degree of voluntary motor control and sensory feedback. In a preferred embodiment, the interface comprises: (a) a multichannel microwire electrode array for acquiring neural signals from large numbers of single neurons comprising: (i) one or more microwire electrodes; (ii) one or more printed circuit boards in electrical connection with the one or more microwire electrodes comprising: (1) one or more conductive traces spaced part about 0.015 inches (center to center) or less; and (2) one or more conductive pads in electrical connection with the one or more conductive traces; and (iii) one or more connectors in electrical connection with the one or more conductive pads and having contacts spaced about 0.030 inches (center to center) or less; (b) an implantable neurochip adapted to communicate with the multichannel microwire electrode array and to filter and amplify the one or more neural signals; (c) a motor command extraction microchip adapted to communicate with the implantable neurochip and embodying one or more motor command extraction algorithms, the microchip and the algorithms adapted to extract motor commands from the brain-derived neural signals; (d) an actuator adapted to communicate with the motor command extraction microchip and to move in response to the motor commands and to acquire sensory feedback information during and subsequent to a movement; (e) a sensory feedback microchip embodying one or more sensory feedback information interpretation algorithms adapted to communicate with the actuator, the sensory feedback microchip adapted to form interpreted sensory feedback information; (f) a structure adapted to communicate with the sensory feedback microchip and to deliver interpreted sensory feedback information to the subject; and (g) one or more power sources adapted to provide power, as necessary, to one or more of the group comprising: the implantable neurochip; the motor command extraction microchip; the actuator; the sensory feedback microchip; and the structure adapted to relay interpreted sensory feedback information to the subject.

Furthermore, an intelligent brain pacemaker for a mammal having a cranial nerve not associated with an autonomic function is disclosed. In a preferred embodiment, the intelligent brain pacemaker comprises: (a) a multichannel microwire electrode array for acquiring neural signals from large numbers of single neurons comprising: (i) one or more microwire electrodes; (ii) one or more printed circuit boards in electrical connection with the one or more microwire electrodes comprising: (1) one or more conductive traces spaced apart about 0.015 inches (center to center) or less; and (2) one or more conductive pads in communication with the one or more conductive traces; and (iii) one or more connectors in electrical connection with the one or more conductive pads and having contacts spaced about apart 0.030 inches (center to center) or less; (b) a seizure detector adapted to detect seizure-related brain activity of a mammal in real-time, the seizure detector being electrically connected to the multichannel microwire electrode array; (c) one or more nerve stimulators adapted to provide electrical stimulation to a mammal's cranial nerve not associated with an autonomic function, to terminate or ameliorate the seizure, the one or more nerve simulators being electrically connected to the seizure detector; and (d) a power source for providing power to the intelligent brain pacemaker.

It is thus an object of the present invention to provide a high-density multichannel microwire electrode array. It is another object of the present invention to provide a method for assembling a high-density multichannel microwire electrode array. These and other objects are achieved in whole or in part by the present invention.

Some of the objects of the invention having been stated hereinabove, other objects will become evident as the description proceeds, when taken in connection with the accompanying Drawings and Examples as best described hereinbelow.

DETAILED DESCRIPTION OF THE INVENTION

I. Definitions

Figure 1A:
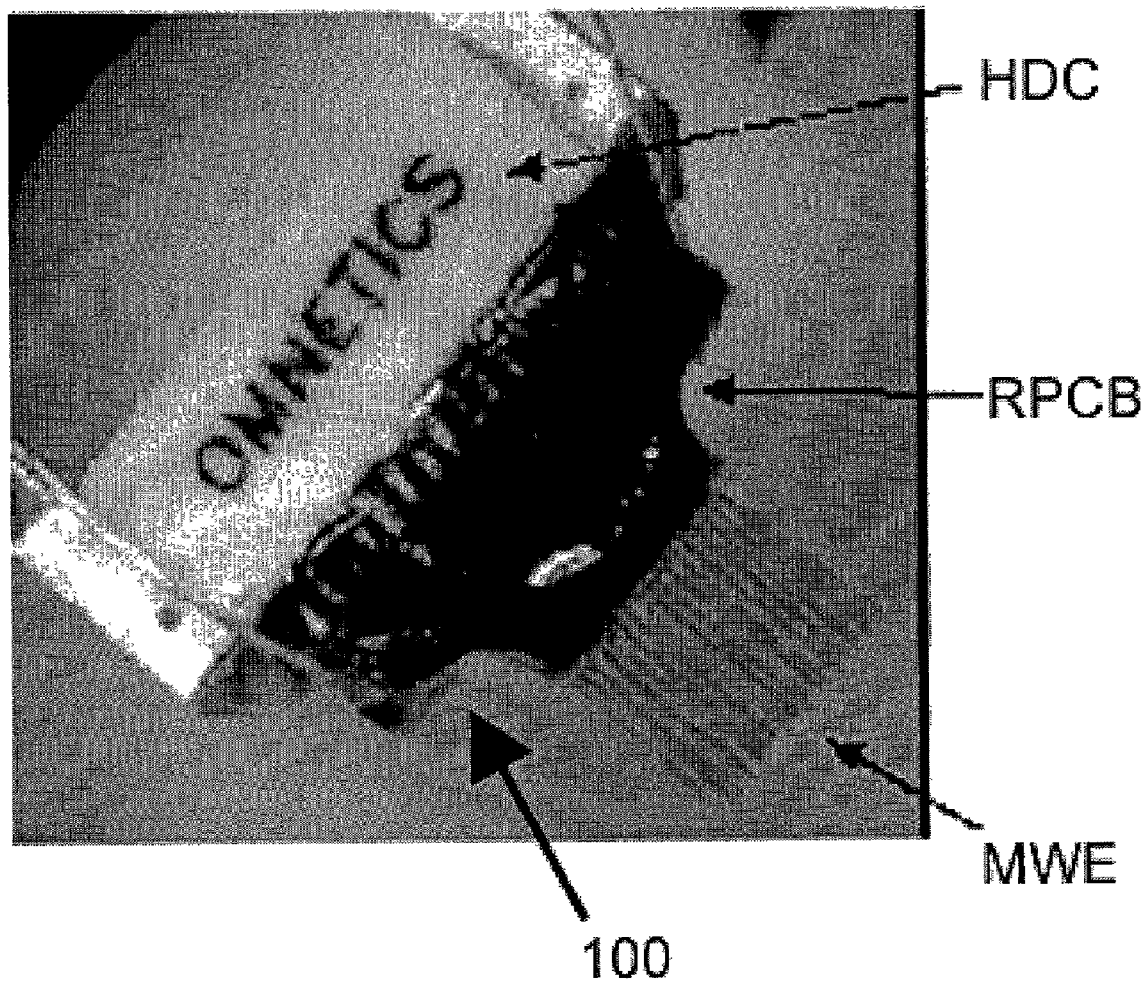
FIG. 1A is a photograph depicting one embodiment of a high-density multichannel microelectrode array of the present invention.

Following long-standing patent law convention, the terms "a" and "an" mean "one or more" when used in this application, including the claims.

As used herein, the terms "actuator", "external device" and "prosthetic limb" are used interchangeably and mean any kind of device adapted to perform a movement. Although an actuator preferably performs a movement in three dimensions, an actuator can also be limited to performing movements in two dimensions. Thus, an actuator can be a manipulandum confined to two-dimensional motion. A preferred actuator comprises a prosthetic limb, which can be fitted on, or integrated into, the body of a subject. An actuator can also be associated with machinery and/or circuitry that allow the actuator to respond to one or more forms of input with one or more movements. It is also preferable that the range of motion of an actuator designated as a substitute for a patient's lost or paralyzed limb be limited to the range of motion of the limb for which the actuator is substituting.

As used herein, the term "conductive paint" means a material that can be applied to a surface and exhibits the property of conductivity when a current is applied thereto. Preferred conductive paints include those comprising noble metals, such as colloidal silver.

As used herein, the term "conductive pad" means a structure comprising a conductive material, such as copper. A conductive pad is also preferably adapted for conductive association (e.g. via soldering) with another structure, such as a contact of a conductor.

As used herein, the term "conductive trace" means a pattern of conductive material disposed on a support. In a preferred embodiment, a conductive trace comprises a pattern of copper disposed and is disposed on a circuit board or a flex circuit.

As used herein, the term "contact" means any structure adapted to transmit a signal therethrough. For example, a contact can comprise a pin or a socket disposed on a connector. Preferred contacts comprise a conductive material and are preferably, but not necessarily, insulated to prevent signal loss.

As used herein, the term "electrode" means an electric conductor through which a voltage potential can be measured. An electrode can also be a collector and/or emitter of an electric current. Preferably, an electrode is a solid and comprises a conducting metal. Preferable conducting metals include noble metals, alloys and particularly stainless steel and tungsten. An electrode can also be a microwire, or the term "electrode" can describe a collection of microwires. Thus, particularly preferred electrodes comprise TEFLON® coated stainless steel or tungsten microwires.

As used herein, the terms "field potential data" and "field potentials" are used interchangeably and typically mean voltage low frequency measurements collected from one or more locations in a subject's brain or nervous system.

As used herein, the term "microwire" means an insulated conductive wire having a diameter of between about 10 and about 75 μm. Preferably, a microwire is insulated, and is more preferably TEFLON® coated.

As used herein, the term "microwire array" means a collection of two or more microwires, the microwires having a first and a second end. The first end of a microwire is preferably, but not required to be, adapted to interact with neural tissue and the second end is preferably disposed in electrical communication with a printed circuit board or flex circuit adapted to coalesce signals acquired by each microwire of a microwire array. Preferably the second end of the each microwire is maintained in a fixed spatial relationship with other microwires of the microwire array.

As used herein, the term "motor command" means one or more neural signals associated with the control of one or more muscles or muscle groups of a subject. Motor commands are generally formed in the brain or nervous system of a subject and these commands control movements executed by the muscles of the subject. Movements preferably comprise voluntary movements, however movements can also comprise involuntary movements.

As used herein, the term "nerve stimulator" means any device or means adapted to stimulate one or more nerves. Stimulation imparted by a nerve stimulator can be of an electrical, optical or physical nature, however electrical stimulation is preferred.

As used herein, the term "neural signal" means a signal, which can take any form, originating in the nervous system of an organism.

As used herein, the term "neurochip" means any microchip adapted for implantation in the body of an organism. Preferably, a neurochip is adapted to be implanted in the nervous system of an organism.

As used herein, the terms "operator", "patient" and "subject" are used interchangeably and mean any individual monitoring or employing the present invention, or an element thereof. Operators can be, for example, researchers gathering data from an individual, an individual who determines the parameters of operation of the present invention or the individual in or on which a high-density multichannel microelectrode array is disposed. Broadly, then, an "operator", "patient" or "subject" is one who is employing the present invention for any purpose. As used herein, the terms "operator", "patient" and "subject" need not refer exclusively to human beings, but rather the terms encompass all organisms having neural tissue.

As used herein, the terms "printed circuit board" and "PCB" are used interchangeably and broadly mean any structure comprising at least one conductive trace. A printed circuit board (PCB) can comprise multiple layers, such as a conductive layer covered with an insulating layer. A PCB can also comprise a third layer on top of the insulating layer, creating a conductor-insulator-conductor sandwich structure.

A PCB need not be manufactured by an imprinting process. For example, a PCB can be manufactured by an etching process and can still be a PCB. The term "printed circuit board" is used in its broadest sense and refers to a structure, which is preferably planar, that comprises one or more conductive structures. A PCB can be flexible or rigid.

As used herein, the terms "sensory feedback", "sensory feedback information" and "sensory feedback data" are used interchangeably and mean any form of data relating to the perception by, or interaction between, an actuator and an object. Sensory feedback can take the form of tactile information such as shape, hardness and brittleness or sensory feedback can take the form of temperature information, such as hot or cold. Tactile information can also relate to the amount of force applied by an actuator to an object.

II. General Considerations

In one aspect of the present invention, neural signal data are acquired from large numbers of single neurons. Neural signal data are measurements of the electrical activity and other activity in an area or region of the brain or other organ. Collecting data from large numbers of single neurons is a different process from collecting field potentials from a region of a subject's brain or other neural tissue. However, both types of data (field potential data and data from a large number of single neurons) can be collected by employing an array of the present invention.

By way of example, when an individual monitors a field potential (i.e. the amplitude of a field potential) at a point on the surface of the cerebral cortex, for example, what is detected is the overlapping summation of electric fields generated by active neurons in the depths of the cerebral cortex, which have spread through the tissues and up to the surface. These nerve cells can be characterized as point dipoles that are oriented perpendicular to the surface of the cerebral cortex. In other words, each cell has a current source where positive charge moves outwardly across its membrane and a current sink where the same amount of positive charge moves inwardly at each instant. Thus, the flow of current across each cell establishes an electric field potential that is equivalent to the electrostatic field potential of a pair of point charges, one positive at the location of the current source and one negative at the current sink. The amplitude of this field potential, i.e., the electric field strength, decreases inversely with distance in all directions from each point charge, and is relatively low at the surface of the cerebral cortex.

When many nerve cells are generating field potentials in a given region, these field potentials sum and overlap in the neural tissue, in the extracellular fluid, and at the brain surface. This summation is a linear function in this volume conductor, since the field strength of a given cell varies inversely as a function of the distance from each current source or sink. Thus, if the electric potential of a given region is measured at a sufficient number of points and depths, it is possible to deduce the locations and amplitude of each dipole generator at any instant of time.

In contrast with recording field potential data, recording single neuron data involves measuring, in relative isolation, the electric voltage potential of an individual neuron that results when the electric charges flow into and out of the cell. This is commonly achieved by positioning the exposed tip of a microwire recording electrode into close proximity with an individual neuron. In this situation, the electric signal that results when current flows into or out of the neuron closest to the microwire is much greater in amplitude than the signal that is generated by other neurons further from the microwire. The signals of differing amplitudes can then be separated using various signal processing techniques. By positioning many recording microwire electrodes into a region of neural tissue, it is possible to isolate and record the electric activity of many individual neurons simultaneously.

Lower density electrode arrays are problematic because they are severely limited in the amount of information they can gather. The miniaturized, high-density, multichannel electrode array described herein provides a significant increase in the density of implantable electrodes for neurobiological research or clinical applications. The electrode array design (described below) uses state of the art printed circuit board design and miniaturized connector technology to improve the density of implanted electrodes by at least an order of magnitude to about 320 electrodes per square centimeter.

III. Basic Components of a High-Density Multichannel Microwire Array

A high-density multichannel microwire array of the present invention comprises at least three basic components. First, a high-density multichannel microwire array of the present invention comprises an array of microwire electrodes. A high-density multichannel microwire array of the present invention further comprises a printed circuit board to which the microwire electrodes are connected. Additionally, a high-density multichannel microwire array of the present invention comprises a high-density, miniature connector that communicates with the printed circuit board. Each of these components is discussed further in the sections that follow.

Figure 1B:
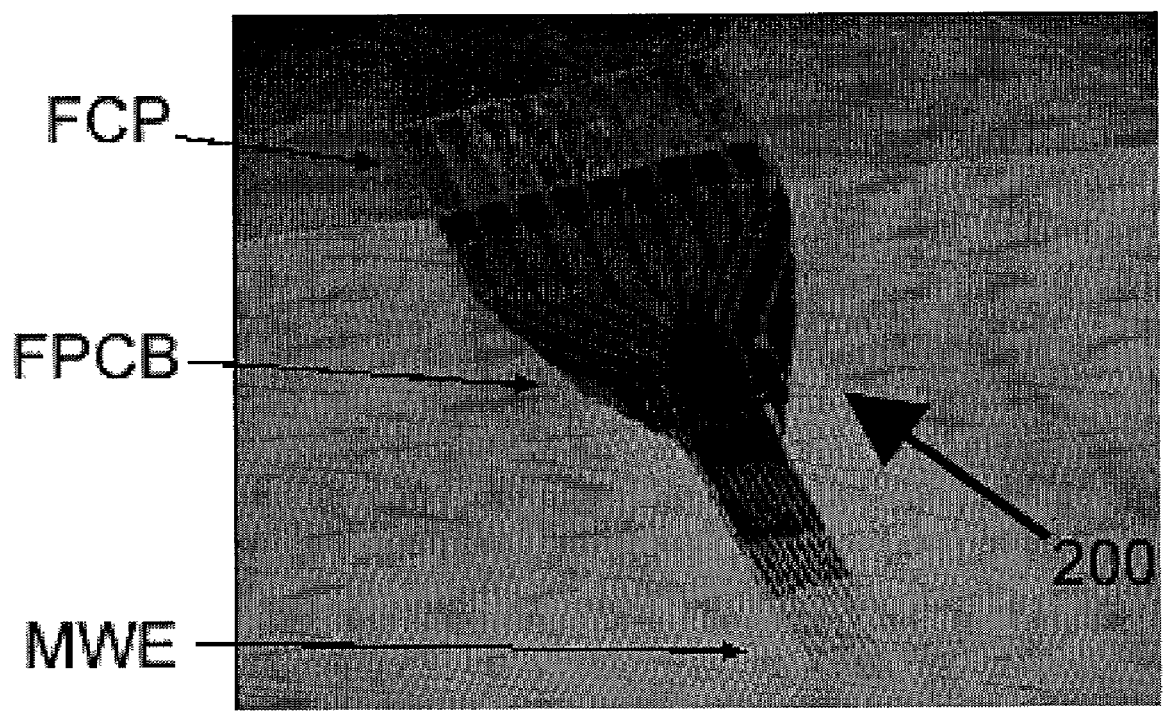
FIG. 1B is a photograph depicting another embodiment of a high-density multichannel microelectrode array of the present invention.

FIGS. 1A and 1B depict two overall configurations 100 and 200, respectively, of an electrode array of the present invention. First, FIG. 1A depicts microwire electrodes MWE associated with printed circuit board RPCB. Printed circuit board RPCB is then associated with high-density connector HDC. The array depicted in FIG. 1A comprises a more rigid PCB, which has a thickness of about 0.08 inches. The entire assembly 100 is potted with dental acrylate to seal the assembly.

In another embodiment, a second type of array 200 is shown in FIG. 1B. This type of board is similar to the board depicted in FIG. 1A except that it is made from flexible, rather than rigid, material. Referring to FIG. 1B, flexible printed circuit board FPCB is labeled. Flexible printed circuit board FPCB has a thickness of about 0.01 inches. The flexibility of this board facilitates implantation of electrodes in certain circumstances where an end adapted to receive a connector can be offset slightly from the plane of one or more microwire electrodes that are associated with printed circuit board PCB.

Figure 4A:
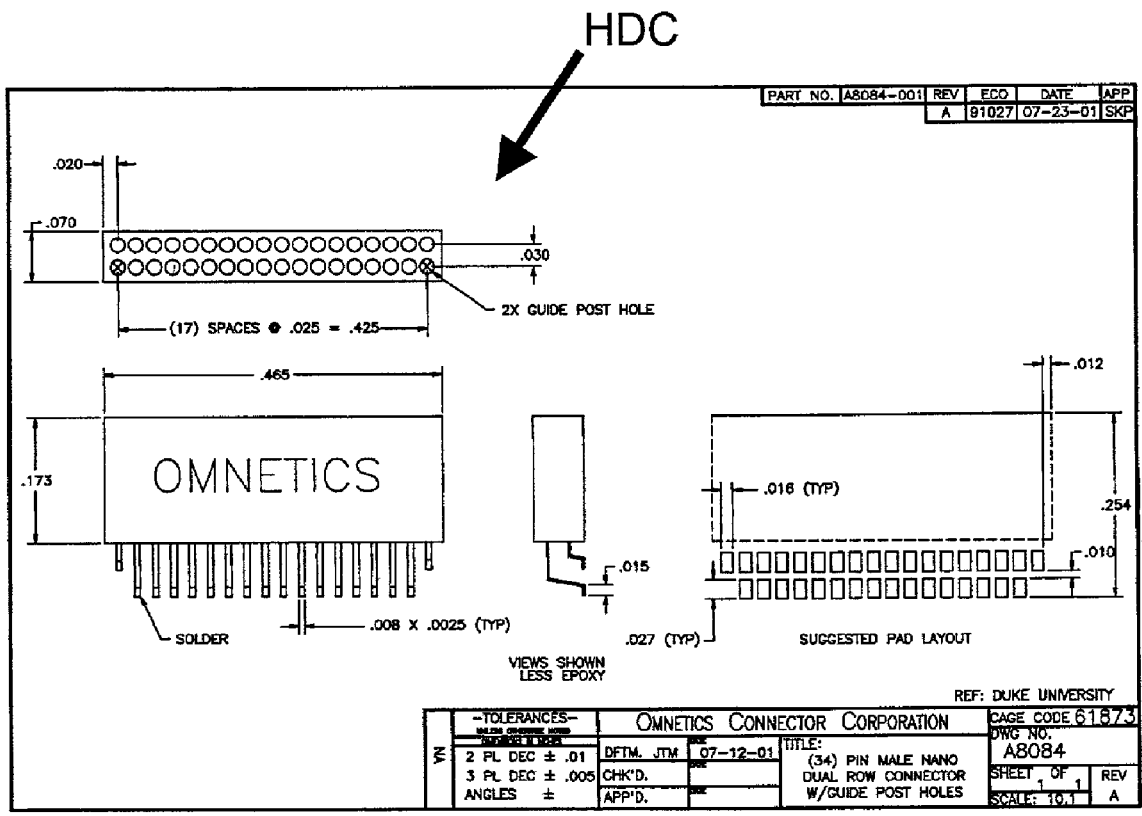
FIG. 4A is a schematic diagram of a high-density connector that can be employed to connect one or more electrode arrays with an external device.
Figure 4B:
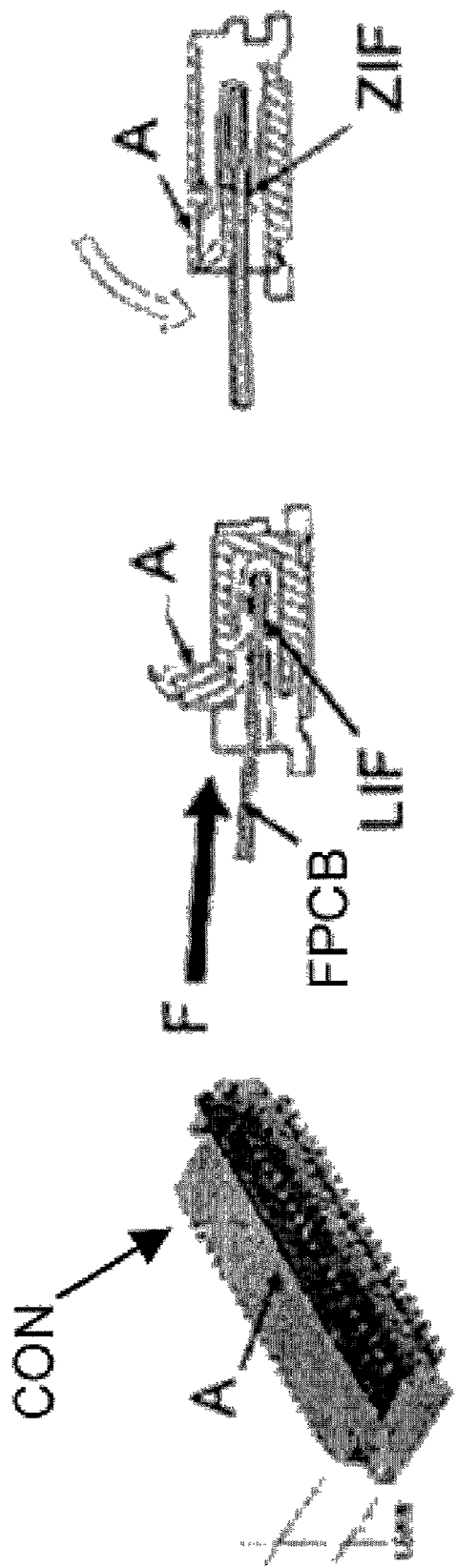
FIG. 4B is a schematic diagram of a high-density connector that can be employed to connect one or more electrode arrays with an external device.

Additionally, in this embodiment 200 of the invention, the exposed traces on printed circuit board FPCB terminate at contact pads FCP, which are distal from microwire electrodes MWE. Contact pads FCP are adapted for association with a high-density connector, particularly a zero insertion force (ZIF) connector, as depicted in FIG. 4B and discussed hereinbelow.

III.A. Array of Microwire Electrodes

In one aspect of a high-density multichannel microwire array, real-time measurements of electrical neural signals can be acquired from large numbers of single neurons in the brain or neural tissue of a subject. The acquisition of real-time measurements permits the real-time evaluation and analysis of data. Thus, real-time data acquisition and analysis enables an ongoing evaluation of data in the same time frame as the data is acquired. When real-time data acquisition and analysis is performed, there is no delay between data acquisition and the ability to access, analyze and evaluate the acquired data.

As disclosed hereinbelow, the present invention makes possible a greater volume of real-time data acquisition measurements than previously possible. In one example, the present invention discloses the use of microwire electrode arrays to acquire neural signals in real time. Microwire arrays are preferred for the acquisition of neural signal data.

In the context of the present invention, neural signals are conducted by electrodes to a terminus, where the signals are collected. Therefore, suitable electrodes for practicing the present invention are conductive and, if the electrodes are to be implanted in the tissue of subject, biocompatible with a body and tissues of the subject. Stainless steel microwires and tungsten microwires are particularly preferred electrodes, although electrodes can be fashioned from many different materials, including noble metals and conductive polymers. It is also preferable that the stainless steel and tungsten wires are jacketed with an insulating material while leaving at least one segment of the wire exposed for acquisition and transmission of electrical signals. Preferred insulating materials include polytetrafluoroethylene (marketed as TEFLON® by DuPont, Inc., of Wilmington, Del.) and S-Isonel.

III.A.1. Preparation of Microwire Electrodes

Microwire electrodes can be employed in the present invention to detect electrical activity in large numbers of single neurons in the brain or neural tissue of a subject. Such microwire electrodes can be arranged to form an array. In a preferred embodiment a microwire array comprises a plurality of stainless steel or tungsten microwires. Preferably, the microwires have a diameter of about 10 $\mu$m to about 75 $\mu$m, with a diameter of about 50 $\mu$m being preferred. This size makes them suitable for implantation with a minimum of tissue disruption. Suitable microwires can be manufactured using standard wire pulling techniques or can be purchased commercially from a vendor, such as NBLabs of Denison, Tex. Suitable microwire electrodes can be formed of any conductive material, such as stainless steel, tungsten conductive polymers and noble metals, to name just a few representative materials.

When the microwire electrodes are to be implanted in the brain tissue of a subject, it is preferable to partially coat the exterior of the microwire electrodes with polytetrafluoroethylene (marketed under the trade name TEFLON® by DuPont, Inc. of Wilmington, Del.), S-Isonel or other insulating material. TEFLON® coating of the microwire electrodes offers a degree of insulation for the microwires, which not only isolates the surrounding tissue from the microwire material but also permits a more spatially-focused acquisition of data. Coating the microwires offers the additional advantage that electrical data can be acquired exclusively from that area of the microwire that is not coated (i.e. the non-insulated cross-sectional area at the end of the implanted end of the microwire electrode).

III.A.2. Microwire Electrode Arrays

Microwire arrays useful for acquiring data from large numbers of single neurons can be formed generally as follows. Initially, a plurality of suitable microwires, such as those disclosed herein, are provided. Microwire electrodes have first and second ends: the first end is defined as the end of the electrode that, when emplaced, contacts the brain or neural tissue, while the second end of the electrode ends at a terminus such as a printed circuit board.

Any number of microwire electrodes can be employed to form a microwire array. It is also preferable, but not required, that the second end of each microwire electrode be fixed in a definite spatial relation to the second ends of other microwire electrodes. This arrangement can be conveniently maintained by employing a printed circuit board with which each second end is associated. Although the second end of a microwire electrode can be associated with a printed circuit board, the first end preferably remains flexible, thus facilitating placement at a range of locations. Methods of associating microwires with a printed circuit board are disclosed hereinbelow.

Thus, a microwire electrode array preferably comprises a plurality of microwire electrodes having free and flexible first ends, while having second ends oriented in a particular spatial arrangement. An advantage of the orientation of the second ends of the microwire electrode is that electrical neural signals can be recorded in a channel-specific fashion, due to the ability to easily correlate the position of a microwire electrode in situ with the position of the second end of the microwire electrode in the terminus (e.g. the printed circuit board).

It is preferable that each microwire electrode be monitored on its own channel, so as to avoid a global average of signals for all of the microwire electrodes. By monitoring each electrode on its own channel, it is possible to simultaneously monitor a variety of regions of tissue in a single subject's brain.

III.B. Printed Circuit Board

Figure 2:
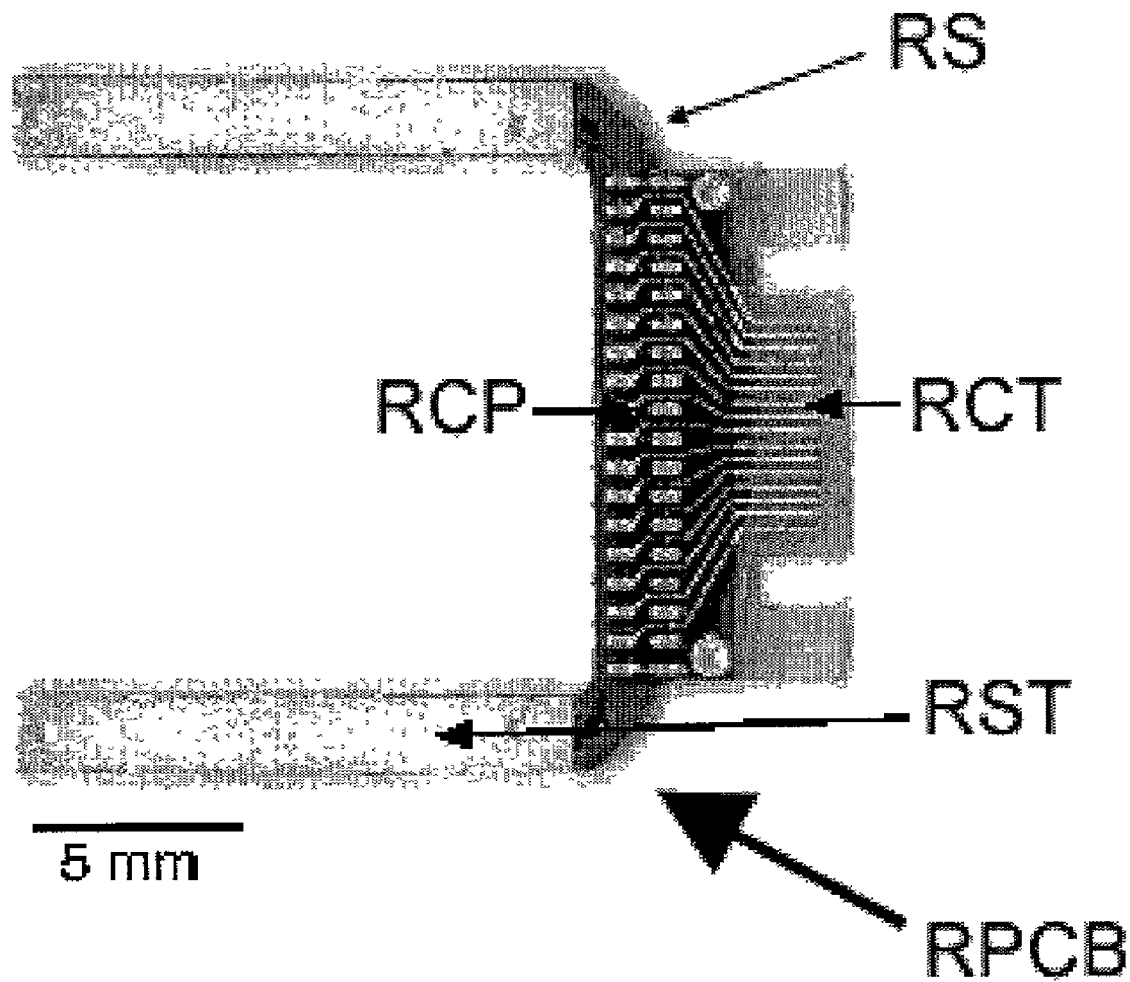
FIG. 2 is a photograph depicting a rigid printed circuit board showing the components of the board.

A high-density multichannel microelectrode array of the present invention comprises a printed circuit board (i.e. a PCB). The PCB can be custom made for the electrodes described above. Turning now to FIG. 2, one board type (RPCB) employs rigid substrate RS and is preferably about 0.08 inches thick. Conductive traces RCT can be etched onto the board. Alternatively, a laminate, such as a sheet of copper, can be associated with a rigid board and regions of copper etched away to leave conductive traces RCT. Conductive traces RCT are preferably about 0.004 inches wide and preferably spaced about 0.012 inches from each other (center to center) at an end at which microwire electrodes are attached.

The individual microwire electrodes can be communicatively associated with the PCB by employing a custom made jig (as described hereinbelow). After the association, the microwire electrodes will be in electrical contact with the individual traces.

Continuing with FIG. 2, conductive traces RCT extend from the electrode wires and terminate at a region of conductive pads RCP. Each of conductive traces RCT terminates with one or more of conductive pads RCP. Conductive pads RCP are labeled in FIG. 2.

In the embodiment depicted in FIG. 2, RPCB comprises 2 long removable support tabs RST. Removable support tabs RST can be employed for mechanical support of RPCB during assembly of the electrodes. They can also be employed to hold the electrode assemblies during surgical implantation. Removable support tabs RST can be removed once the electrodes are implanted. FIG. 2 depicts a preferred location of support tabs RST.

Figure 3:
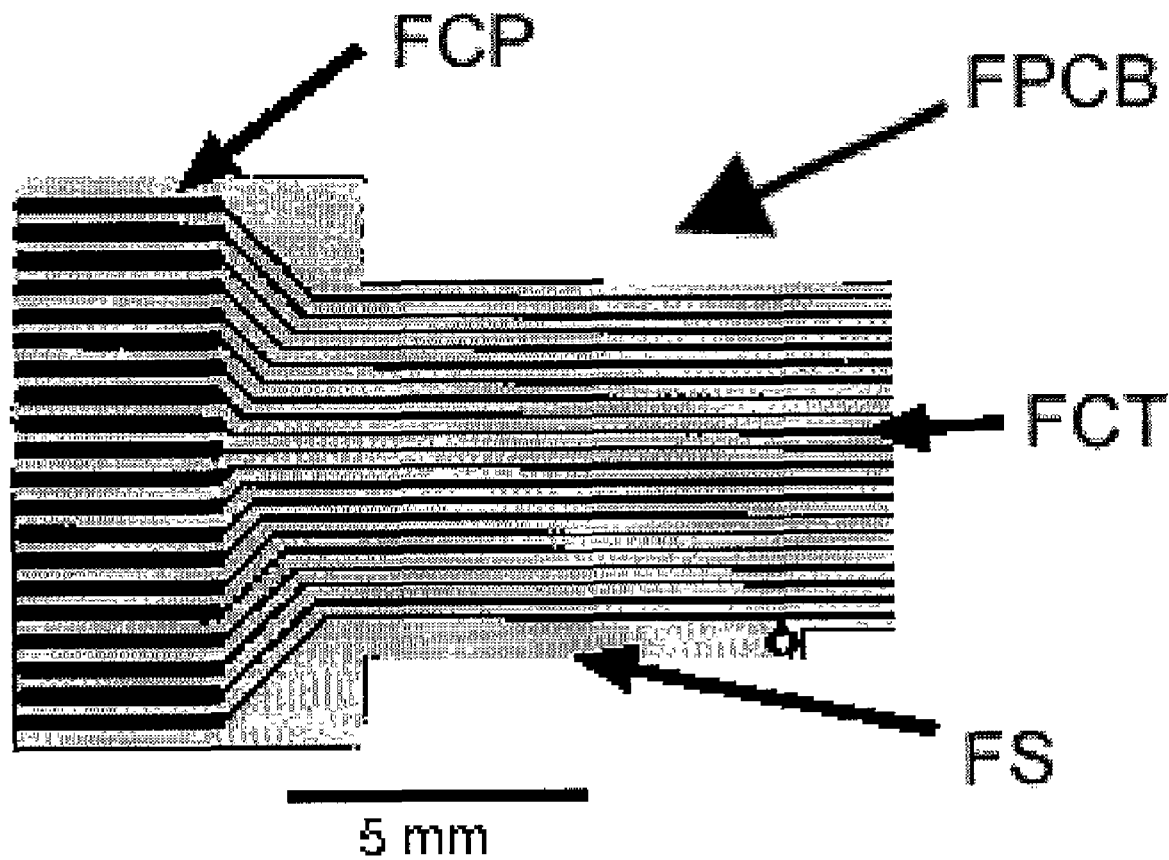
FIG. 3 is a schematic diagram of a flexible printed circuit board showing the components of the board.

Referring next to FIG. 3, another preferred PCB architecture (FCPB) is depicted. FCPB comprises flexible substrate FS. Flexible substrate FS is preferably about 0.01 inches thick. Conductive traces FCT are disposed on flexible substrate FS. Conductive traces FCT terminate with flexible contact pads FCP. Contact pads FCP can be arranged and spaced so as to coincide with the spacing of a zero insertion force (ZIF) connector (see FIG. 4B), which is a preferred high-density connector.

III.C. High-Density Connector

High-density multichannel microwire electrode arrays 100 and 200 of the present invention can each also comprise a connector. A connector is preferably adapted to interface between a PCB and an external device, such as a signal processing or storage apparatus. Preferably, the connector comprises a contact for each conductive trace and conductive pad of the PCB. Preferably, the connector is a high-density connector.

A wide range of connectors can be employed in the present invention. For example, the high-density connector HDC shown in FIG. 1A is custom manufactured by Omnetics Corporation of Minneapolis, Minn. The contact spacing in this connector is 0.025 inches. The particular connector HDC seen in FIG. 1A comprises a dual row connector with 18 contacts per row. These connectors attach to the RPCB via surface mount solder pads. These connectors are very rugged, extremely compact, very high-density connectors. FIG. 4A is a schematic representation of connector HDC depicted in FIG. 1A. Surface mount solder pads RCP are depicted in FIG. 2.

Different numbers of contacts can be employed with different numbers of electrodes. For example, an electrode array comprising 8 wires can interface with a connector comprising 9 contacts: 8 for each of the 8 microwires and the $9^{th}$ contact for a ground connection. Electrode arrays comprising 32 electrodes can employ connector HDC as depicted in FIG. 4A.

FIG. 4B depicts a different kind of connector that can be employed in the present invention, namely a ZIF connector. This type of connector is preferably employed when the PCB is FPCB (see FIG. 1B). Referring to FIG. 4A, connector CON is depicted. Connector CON comprises an actuator A. In operation, flexible printed circuit board FPC is inserted into a slot in connector CON by applying force F to the PCB as indicated in the figure. Actuator A is open at this point. When fully inserted, flexible printed circuit board FPCB is in contact with low insertion force structure LIF. Structure LIF comprises conductive material that contacts the conductive pads of FPCB. After flexible printed circuit board FPCB has been fully inserted, actuator A is lowered. This action secures that contact between flexible circuit board FPCB and low insertion force structure LIF, as well as forming a contact between flexible circuit board FPCB and zero insertion force structure ZIF. Summarily, when the operation is complete, conductive pads FCP of flexible circuit board FPCB are in electrical connection with the contacts of connector CON.

IV. Assembling a High-Density Microwire Electrode Array

A high-density microwire electrode array of the present invention can be assembled via the following general steps. It is noted that additional steps can be added to this general procedure and/or the recited steps can be modified. Such deviations from the recited assembly method remain within the scope of the present invention.

Short lengths of electrode microwires can be pre-cut. As noted hereinabove, microwires can comprise a material selected from the group consisting of stainless steel, tungsten, noble metals, alloys and conductive polymers, to name just a few preferred materials. The microwires can be of any dimension, although preferred microwires have a diameter of about 50 $\mu$m or less. The microwires are preferably coated with an insulating material, such as S-Isonel or TEFLON®. The insulating material preferably insulates the microwires along their entire length with the wires being exposed only at the cut ends.

An optional jig can be employed to hold the electrode microwires in a desired alignment (e.g. a parallel alignment) and to align the wires with conductive traces on one or more PCBs. The jig can be helpful in associating microwires with a PCB. When a jig is employed, the wires can be threaded into the jig on one end and a PCB can be plugged into the other end. PCBs that comprise a rigid material (RPCB) can have a connector already soldered onto the appropriate pads. Flexible PCBs (FPCB) typically do not have any connectors pre-attached.

A preferred jig employs a drilled array that is consistent with the PCB thickness and conductive trace spacing. With the wires threaded into the array and a PCB plugged in to the opposite side, a small bead of adhesive (e.g. cyanoacrylate gel) is laid down along the edge of the PCB. The wires are then placed in contact with corresponding conductive traces as established by the array. This completes the mechanical connection from the electrode wires to the connector. An electrical connection to the wires is formed by applying a highly conductive colloidal silver paint to both the exposed end of the microwire and it's respective conductive trace. Once the paint is dry, the electrode assembly is unplugged from the jig and the wires can be cut to length, preferably about 8 mm long, however, different lengths can employed for different implant procedures. For example, longer microwires might be desirable when the array is employed to acquire neural signals from structures that are located deep inside a subject's brain. A new PCB can then be plugged into the jig and the process repeated until the jig is expended of its wire. A variable number of electrode assemblies can be produced with the jig fully loaded. When the assembly process is complete, the completed array can be removed from the jig.

Figure 5A:
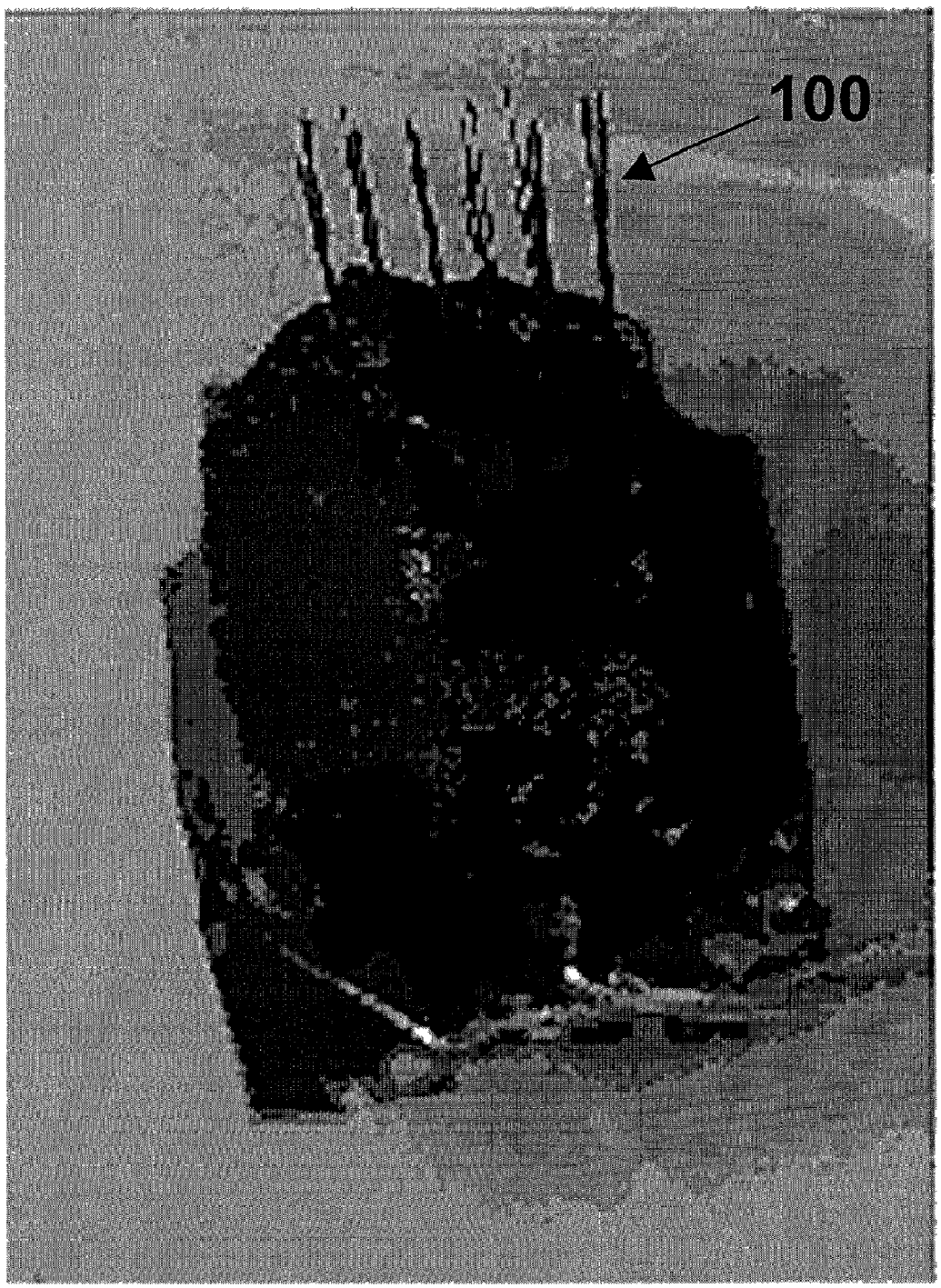
FIG. 5A is a photograph depicting an array of 6 rows of 8 electrodes per row for a total of 48 electrodes.

After the electrode assembly is removed from the jig, ground wires are preferably attached to ground pads on the PCB. Subsequently, the assembly can be potted in a desired compound (e.g. dental acrylic compound) in order to seal and protect the assembly. The electrode assembly is then ready for use. A completed array is depicted in FIG. 5A.

If an electrode assembly is to have more than one row of microwires, multiple PCBs can be employed. Each row of microwires can be associated with a PCB as disclosed above. The microwire-PCB assemblies are then joined together to form an assembly comprising multiple rows of microwires and associated PCBs (see FIG. 5A).

A guide can be employed to assist in the placement of multiple rows in a small area. The guide can be loaded with the single row assemblies and the PCBs of the single rows glued together. By employing this approach, any number of rows of wires can be assembled to form large arrays of microwire electrodes.

V. Surgical Implantation of an Assembled Microwire Electrode Array

The electrodes of the intelligent brain pacemaker can be implanted directly in the brain tissue of a subject. The exact positioning (i.e. location and depth) of each electrode can be critical and can be determined based on known coordinates. For example, suitable coordinates for placement of electrodes in a rat brain are disclosed in Paxinos & Watson, (1986) *The Rat Brain*, Ed. 2. New York, Academic, Harcourt, Brace and Jovanovich. When microwires are employed as electrodes, implantations can be made by performing craniotomies in the areas in which electrodes are to be implanted. Craniotomies and implantations can be performed using standard surgical techniques. See, e.g., Nicolelis et al., (1997) *Neuron* 18: 529–537, incorporated herein by reference.

When microwires are implanted to serve as electrodes, the microwires can be implanted in any region of a subject's brain or other neural tissue. When electrodes are to be implanted in the brain tissue, however, it is preferable that the electrodes be implanted in the primary somatosensory cortices (SI) and/or other regions of the subject's brain. When the primary somatosensory cortices are selected as an electrode placement site, it is preferable that the electrodes be implanted in layer V of the cortices. The precise location of implantation can be determined by the ultimate purpose for performing the implantation. For example, if it is desired to record motor control signals, implants (e.g. microwire electrodes) can be placed in motor cortical areas of a subject's brain.

Figure 5B:
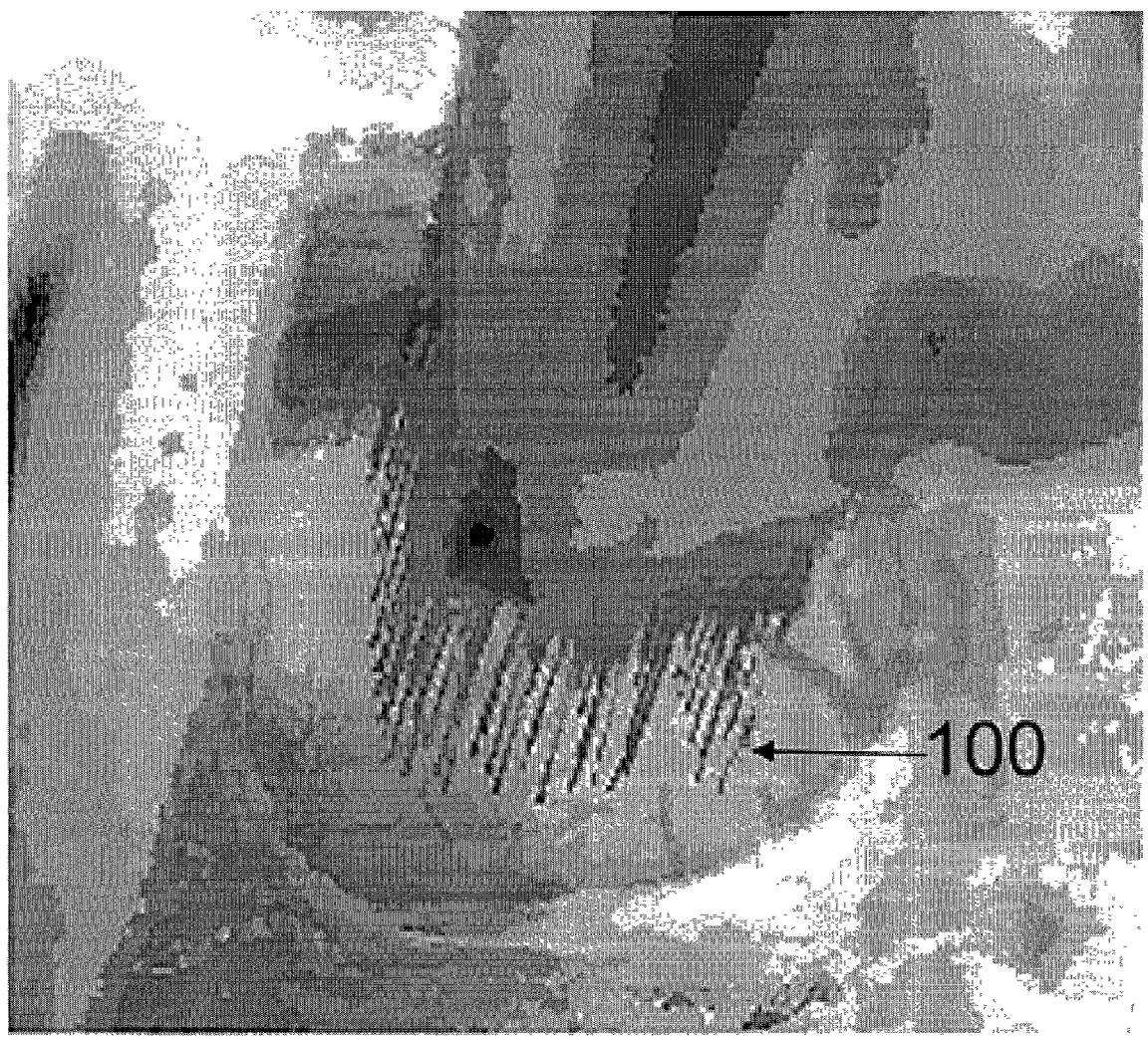
FIG. 5B is a photograph depicting an array of 8 rows of 16 electrodes per row for a total of 128 electrodes wherein the array is about to be implanted into the cerebral cortex of a Rhesus monkey.

Employing the following steps, which can be varied at the discretion of the individual implanting the electrodes, electrodes can be implanted in the brain or neural tissue of a subject. Initially, the subject is anesthetized. Craniotomies can then be made in the skull of the subject and the electrodes lowered into the tissue. Various readings can be acquired during the implantation procedure to ensure that the electrodes are placed at the proper depth in the tissue. The precise positioning for each craniotomy can be determined by evaluating coordinate maps, prior to insertion of the electrodes. When the electrodes are properly emplaced, they can be held in place by skull screws, a suitable cement or combinations thereof. Polyethylene glycol, sucrose or another biocompatible material, can be employed to coat a microwire before it is inserted into a subject's neural tissue. This practice can assist in the insertion process and is not harmful to the subject, since the material itself is eventually removed from the inserted microwire by mechanisms of the subject's body. FIG. 5B is a photograph of a stack of microwire array 100 of the present invention being inserted into the brain of a Rhesus monkey. The array shown in FIG. 5B comprises a plurality of stacked microwire arrays 100.

VI. Applications of the Present Invention

A critical problem in the field of neurobiological research that limits the ability to study neuronal function or to treat neural pathologies is the inability to record data simultaneously from large numbers of single neurons from relatively small regions in the brain. The electrode arrays 100 and 200 of the present invention provide a significant improvement over existing electrode technologies, effectively increasing the density of implantable electrodes by about an order of magnitude. Use of these electrodes in basic research provides a way of addressing several fundamental questions regarding large scale neural function that, prior to the present disclosure, have been inaccessible to existing technologies.

The present invention can be employed in a range of applications. Broadly, the invention can be employed in any situation in which it is desirable to acquire neural signals, particularly electrical signals, from the brain or neural tissue of a subject. The neural signals acquired by an array of the present invention can then be amplified and/or processed and employed as a component in various applications. A representative but non-limiting list of applications in which the electrode arrays of the present invention can be employed is presented hereinbelow.

VI.A. A High-Density Multichannel Microwire Electrode Array Adapted to Acquire Neural Signals from Large Numbers of Single Neurons In one application of the present invention, a multichannel microwire electrode array (100 and 200) for acquiring neural signals from large numbers of single neurons is disclosed. This array can form a component of a larger system, such as a system adapted to detect and/or treat epilepsy or other neurological condition. The array can also be employed in a system adapted to impart the ability to control the movement of one or more of a subject's appendages, particularly when the subject has been paralyzed or has otherwise lost a degree of motor control.

A microwire electrode array of the present invention (100 and 200) presents several advantages over prior art electrode arrays. For example, a microwire array of the present invention is a high-density array. When the PCBs are arranged in a stacked arrangement, the arrays disclosed herein can accommodate an unlimited number of microwire electrodes. Thus, the quantity and quality of data (e.g. neural signals) that can be acquired by the present arrays greatly exceeds levels presently achievable with prior art electrode arrays.

The PCB design itself is an advance over the prior art. The conductive traces of the PCB are spaced closer together than are the conductive traces of prior art PCBs. This facilitates the association of a greater number of microwire electrodes with a PCB of the present invention than can be accommodated by prior art PCBs and arrays.

Each conductive trace of a PCB can be employed as a single channel. Thus, neural data can be acquired from one location within the brain or other structure of a subject and treated separately from data acquired from another location. Therefore, each conductive trace, and the microwire or microwires associated with that trace, represent a single channel. It is specifically noted that more than one electrode can be associated with a given conductive trace.

The architecture of arrays 100 and 200 of the present invention is different from those prior art electrode arrays that do not feature multiple channels. Prior art electrode arrays typically gather many signals from many locations on one channel, and therefore provide a global average of signals. If the electrodes of these prior art devices are implanted in different regions of a subject's brain, it is not possible to discern the precise origin of a given signal or signals. Consequently, many prior art devices are not adapted to acquire large amounts of data from single neurons, nor can these devices particularly identify the origin of a signal within the brain of a subject.

Additionally, the design of the arrays of the present invention can include a high-density connector HDC. Although high-density connectors are known, until the present disclosure, it was not possible to employ them in an array adapted to acquire neural signals. This was mainly due to the inability to interface the connector with the microwire electrodes. The present invention, however, solves this problem by disclosing a microwire electrode array comprising a high-density connector, as discussed hereinbelow In a preferred embodiment, each high-density microwire electrode array 100 and 200 comprises one or more microwire electrodes. A microwire array preferably comprises a plurality of stainless steel or tungsten microwires. Preferably, the microwires have a diameter of from about 10 µm to about 75 µm. More preferably, the microwires have a diameter of about 50 µm. These dimensions make the microwires suitable for implantation with a minimum of tissue disruption. Microwires can be manufactured using standard wire pulling techniques or can be purchased commercially from a vendor, such as NBLabs of Denison, Tex. Microwire electrodes can be formed of any conductive material, such as stainless steel, tungsten, conductive polymers and noble metals, to name just a few preferred materials.

When the microwire electrodes are to be implanted in the brain tissue of a subject, it is preferable to partially coat the exterior of the microwire electrodes with polytetrafluoroethylene (marketed by DuPont, Inc. of Wilmington, Del. under the trade name TEFLON®), S-Isonel, polymers, plastics and other non-conductive or other insulating material. Coating the microwire electrodes with an insulating material offers a degree of insulation for the microwires, which not only isolates the surrounding tissue from the microwire material but also permits a more spatially-focused acquisition of data. Coating the microwires offers the additional advantage that electrical data can be acquired exclusively from that area of the microwire that is not coated (i.e. the non-insulated cross-sectional area at the end of the implanted end of the microwire electrode).

Continuing with the preferred embodiment, each microwire electrode array 100 and 200 of the present invention comprises one or more printed circuit boards in electrical connection with the one or more microwire electrodes, the one or more printed circuit boards comprising one or more conductive traces spaced apart about 0.015 inches (center to center) or less; and one or more conductive pads in electrical connection with the one or more conductive traces.

At least two different forms of printed circuit board can be employed in the present invention. First, a flexible printed circuit board (FPCB) can be employed. An FPCB is preferably about 0.01 inches thick. As noted above, the flexibility of the FPCB facilitates implantation of electrodes in certain circumstances when it is desirable that the connector end be offset slightly from the plane of the electrode array. Also, with this particular design of FPCB, the exposed traces on the end of the FPCB opposite from the electrodes (see FIGS. 1B & 3) form the male conductive pads for a Zero Insertion Force (ZIF) connector (see FIG. 4B). The spacing of these conductive pads located at the edge of the board preferably coincides with the spacing of the ZIF connector mate.

In another form of printed circuit board, the RPCB is more rigid. A rigid RPCB is preferably about 0.08 inches thick. In this embodiment, the conductive traces, with which microwire electrodes can be associated, originate at one location and terminate at another location in conductive pads. The contacts of a high density connector can be associated (e.g. soldered) with the conductive pads. See FIGS. 1A and 2. FIG. 4A depicts a preferred connector for use with a rigid PCB.

Continuing with the preferred embodiments, an array of the present invention also comprises one or more connectors in electrical connection with the one or more conductive pads and having contacts spaced apart about 0.030 inches or less. As noted, high-density connectors that are commercially available (e.g. the Nano series of connectors available from Omnetics Corp. of Minneapolis, Minn.) can be employed in the present invention. See FIG. 4A. When a flexible PCB is employed, a connector can comprise a ZIF connector, as disclosed in FIG. 4B.

Preferably, the contact spacing is about 0.030 inches or less. Contacts can comprise pins adapted to facilitate an electrical connection between the connector and an external device, such as a signal amplifier or processor. A preferred connector HDC is depicted in FIG. 1A and comprises a dual row connector with 18 connectors per row (see FIG. 4A). These types of connectors have not been employed in microwire electrode arrays, prior to the present disclosure due, in part, to the inability to interface with the microwires. Thus, although such high-density connectors (HDC) have been available, they have not been employed in an apparatus adapted to acquire neural signals.

These connectors can be associated with the PCB via conductive pads disposed on the PCB. Such an association can be an electrical connection that is formed by soldering the contacts (or conductive traces or pads associated therewith) to the conductive pads of a PCB. A connector is preferably very rugged, extremely compact and very high-density.

A connector preferably comprises a number of contacts that is different from the number of microwire electrodes associated with the PCB. For example, an electrode array comprising 8 microwire electrodes employs a connector with 9 contacts: 8 for each of the 8 wires and the $9^{th}$ contact for a ground connection. Thus, it is preferable that a connector comprises at least one contact that serves as a contact for a ground connection.

Variations on the above described array are contemplated and fall within the scope of the present invention. For example, the one or more printed circuit boards can be flexible and somewhat thicker than 0.01 inches thick. The advantages of a flexible PCB (FPCB) are discussed above. Alternatively, it might be desirable to employ a more rigid PCB. In this case, preferred PCBs (RPCB) are substantially rigid and about 0.08 inches thick, although a rigid PCB can be somewhat thicker or thinner than 0.08 inches thick.

An advantage of the present invention is the ability to secure multiple PCBs together in a stack-like arrangement. In this arrangement, the PCBs, can be superimposed on one another and secured together by any desired means, although it is preferred that the PCBs of such an arrangement are secured to one another by glue or other adhesive.

When a stacked arrangement is employed, it is preferable, but not required, to associate microwires, connectors and any other components with the PCBs before the PCBs are secured to one another. An assembly jig can be employed to maintain the spatial position of each PCB while components are associated with the PCB. The same jig, or another jig, can be employed to orient the PCBs relative to one another while a stack is assembled.

A multichannel microwire electrode array can comprise PCBs that comprise one or more removable support tabs. An example of a PCB that comprises a support tab is depicted in FIG. 2. The support tabs are designated RST in FIG. 2. These support tabs can be employed to facilitate manipulation of the PCB during the process of associating microwires and/or connectors with the PCB, and/or the process of securing two or more PCBs to each other.

Continuing with the PCB, preferred PCBs for use with the present invention comprise conductive traces spaced apart about 0.012 inches (center to center). This spacing facilitates the association of a greater number of microwire electrodes with the PCB. This can impart the acquisition of a large number of neural signals. The spacing of the conductive traces on a PCB is variable, but preferably does not exceed 0.015 inches (center to center). The conductive traces can also be substantially insulated as a means of protecting the traces themselves, as well as insulating them from any potentially deleterious or corrosive surroundings.

Turning next to the connector, a connector of the present invention can comprise a zero insertion force (ZIF) or low insertion force (LIF) connector (See FIG. 4B). These embodiments are especially preferred when the PCB is FPCB. In these embodiments, no soldering is required. To form a connection between a PCB and a connector, the PCB is inserted into a slot or other structure on the connector so as to form an electrical connection between the PCB and the connector. Each conductive trace of the PCB contacts one or more contacts of the connector. In some applications, it might be desirable to associate the PCB with the connector by soldering the contacts of the connector to one or more conductive pads disposed on the PCB. A connector for which this might be desirable is disclosed in FIG. 4A.

VI.B. Method of Assembling a Microwire Electrode Array

In another application, a method of assembling a multi-channel microwire electrode array for acquiring neural signals from large numbers of single neurons is disclosed. The assembled array can be employed in a variety of applications, including those disclosed herein. In a preferred embodiment of the method, one or more microwire electrodes are associated (connected) with a printed circuit board comprising conductive traces spaced about 0.015 inches (center to center) or less and conductive pads in electrical connection with the conductive traces to form a PCB-electrode assembly. The close spacing of the conductive traces facilitates the association of a large number of microwire electrodes with the PCB. The association can comprise soldering the microwires to the conductive traces. Alternatively, the associating can comprise bonding the electrodes to the conductive traces with a cyanoacrylate adhesive.

Due to the small size of the microwires and the PCB, aligning the microwires with the conductive traces of the PCB can be challenging. In order to make this association easier, a jig can be employed. The jig can comprise a member with through holes drilled therein. The holes can be dimensioned so as to accommodate one or more microwires. The precise number of holes can vary with the number of conductive traces on a PCB. A jig can further comprise a member upon which a PCB can be supported. This member can be designed to orient the PCB in a position that facilitates the easy association of the microwires with the PCB. Summarily, a jig can be designed and employed to hold the microwires and the PCB in positions that are preferred for the formation of a PCB-electrode assembly. A jig of this design, or a similar design, can also be employed to orient a stack of PCBs during the process of associating multiple PCBs or PCB-electrodes assemblies, as described herein.

A conductive paint can then be applied to the PCB-electrode assembly to form a coated PCB-electrode assembly. The conductive paint fills two roles: first, it ensures that an electrical connection is formed between the microwires and the PCB; second, it acts as a sealant to inhibit the degradation of bond between the microwires and the PCB. Preferred conductive paints include paints comprising colloidal silver.

Additionally, the coated PCB-electrode assembly is associated with at least one connector via the conductive pads disposed on the PCB. Preferably, the connector comprises (i) a contact adapted to electrically connect with each of the conductive pads and (ii) a ground contact. The association between the connector and the conductive pads can be formed by soldering the two entities together. Alternatively, when the PCB is FRCB and the connector is a ZIF or a LIF connector, the association can be formed by contacting the conductive pads of FPCB with the contacts of the connector.

A contact of the connector can comprise a pin, such as those depicted in FIG. 4A. Alternatively, a contact can comprise a socket. Regardless of its architecture, a contact is adapted to facilitate an electrical connection between the PCB and an external device. More particularly, a connector is adapted to interface with an external device, such as a signal amplifier or a signal processor.

In preferred embodiments of the methods, the one or more microwire electrodes comprise a material selected from the group consisting of stainless steel, tungsten, noble metals, conductive alloys and conductive polymers. Additionally, the one or more microwire electrodes are preferably substantially coated with a material selected from the group consisting of TEFLON®, S-Isonel, polymers, plastics and non-conductive materials.

The disclosed method can be employed to associated multiple PCBs or multiple PCB-electrode assemblies. Indeed, this aspect of the present invention is an advantage over prior art devices and methods. Thus, the above steps can be repeated a desired number of times to form a plurality of coated PCB-electrode assemblies. Subsequently, the coated PCB-electrode assemblies can be bonded together before associating the coated PCB-electrode assemblies with a connector. Alternatively, a connector can be associated with each PCB-electrode assembly prior to the bonding of each PCB to another.

After a coated PCB-electrode assembly (or a plurality of associated assemblies) has been formed, the entire assembly can be potted (i.e. sealed) to protect the assembly as well as to insulate the tissue in which the assembly is implanted from unnecessary electrical and physical damage. Preferred potting compounds include dental acrylic compounds. An assembly potted with a dental acrylic compound is depicted in FIG. 1A.

Summarily, a microwire electrode array (100, 200) of the present invention can be assembled as follows. First, short lengths of electrode wires can be pre-cut. As stated above, the wires are preferably either tungsten alloy with an S-Isonel jacket or stainless steel with a TEFLON® jacket. The jacket provides insulation for the wires along their entire length and the wires are exposed only at the cut ends.

A jig can be employed to hold the electrode wires in parallel alignment and to align the wires with the traces on the PCBs. First, the wires are threaded into the jig on one end and the PCB is plugged into the other end. RPCBs that comprise the rigid material have the connector already soldered onto the appropriate pads. FPCBs preferably do not have any connectors attached. The jig employs a drilled array that is consistent with the PCB thickness and trace spacing. With the wires threaded into the array and the PCB plugged in to the opposite side, a small bead of cyanoacrylate gel is then laid down along the edge of the PCB. The wires are then placed on their traces as established by the array. This completes the mechanical connection from the electrode wires to the connector.

The electrical connection to the wires can be formed by employing a highly conductive colloidal silver paint applied to the end of the wire and it's respective copper trace. Once the paint is dry, the electrode assembly is unplugged from the jig and the wires are cut to length, preferably about 8 mm long, however, different lengths can be selected for different implant procedures. A new PCB is plugged into the jig and the process continues until the jig is expended of its wire.

After the electrode assembly is removed from the jig, ground wires are attached to the ground pads of the PCB and the assembly can be potted in a dental acrylic compound. Electrode assembly 100, 200 is then ready for use.

VI.C. Multichannel Microwire Electrode Array Kit

In yet another application of the present invention, a kit is provided. The kit comprises elements that can be assembled to form a high-density multichannel microwire electrode array of the present invention. A preferred multichannel microwire electrode array comprises the following components.

First, the kit comprises one or more microwire electrodes. The microwire electrodes can comprise a material such as those disclosed herein above, for example stainless steel or tungsten microwires. The microwires can be coated with an insulating material, such as TEFLON® or S-Isonel. The lengths of these microwires can vary with the type of tissue and data acquisition process to which the array will ultimately be put.

The kit also comprises one or more printed circuit boards. The PCB(s) comprise both (i) one or more conductive traces spaced apart about 0.015 inches (center to center) or less and (ii) one or more conductive pads in electrical connection with the one or more conductive traces. Preferred PCBs are 0.08 inches thick and substantially rigid, or 0.01 inches thick and flexible. The conductive traces can be disposed on the PCB and coated with an insulating material that, while facilitating electrical conduction through the traces, serves to insulate the traces from other components or tissue in which the array is ultimately implanted. The spacing of the conductive traces is an advance beyond prior art arrays. This close trace spacing, coupled with the ability to associate multiple PCB-electrode assemblies, facilitates the acquisition of a greater number of signals per PCB than was previously possible.

The conductive pads can comprise any conductive material, such as copper. The pads are preferably dimensioned such that a connector can be joined to the PCB to form an electrical connection between the microwires associated with the PCB and the connector itself.

The kit further comprises one or more connectors having contacts spaced about 0.030 inches (center to center) or less. Again, this spacing of contacts, which can be pins, sockets or other structures, facilitates, in part, the acquisition of large numbers of neural signals. Although such connectors are commercially available (e.g. from Omnetics Corp. of Minneapolis, Minn.), prior to the present disclosure, they have not been employed in a microwire electrode array adapted to acquire large numbers of neural signals from single neurons.

V.D. Control of Epileptic Seizures

The high-density multichannel microwire electrode arrays 100, 200 of the present invention can be therapeutically employed to treat or ameliorate a range of neurogical disorders. Disorders that can be treated by employing a microwire electrode array of the present invention include epilepsy.

Various prior art methods and apparatus purport to reduce or eliminate epileptic seizures. See, e.g., U.S. Pat. No. 6,016,449 to Fischell et al.; U.S. Pat. No. 6,061,593 to Fischell et al.; and U.S. Pat. Nos. 5,540,734; 4,702,254; 4,867,164 and 5,025,807 to Zabara. However, these references do not disclose the stimulation of the trigeminal nerve as an aspect of seizure reduction. Nor do these references disclose an automatic stimulation device that provides stimulation only when a seizure is detected. These and other references appear to generally disclose stimulation of the vagus or other nerves, to the exclusion of the trigeminal nerve. Additionally, these and other references disclose continuous, regular and periodic stimulation of a nerve; they do not disclose stimulation of a nerve exclusively during seizure-related activity. Moreover, these references do not disclose bilateral nerve stimulation, which, in the case of vagus nerve stimulation, can be hazardous to a subject's health.

The microwire electrode arrays of the present invention can be employed to acquire neural signals related to oncoming or occurring epileptic seizures. These signals can be processed and can be employed by an intelligent brain pacemaker device adapted to eliminate or ameliorate an epileptic seizure. A central aspect of such a device is a microwire electrode array adapted to acquire the signals to be analyzed. The arrays of the present invention can be employed in this role.

Another application of the arrays of the present invention is in an intelligent brain pacemaker for a mammal having a cranial nerve not associated with an autonomic function. Such a device preferably comprises a multichannel microwire electrode array for acquiring neural signals from large numbers of single neurons. The array itself preferably comprises one or more microwire electrodes. Preferred microwire electrodes are disclosed hereinabove.

The array further comprises one or more printed circuit boards in electrical connection with the one or more microwire electrodes. The PCB(s) preferably comprise one or more conductive traces spaced about 0.015 inches (center to center) or less and one or more conductive pads in communication with the one or more conductive traces. Again, preferred configurations of a PCB are discussed hereinabove.

The intelligent brain pacemaker also comprises one or more connectors in electrical connection with the one or more conductive pads and having contacts spaced apart about 0.030 inches (center to center) or less. Preferred connectors can comprise those disclosed hereinabove. Alternatively, a connector can be designed and fabricated based on the preferred connector properties disclosed hereinabove.

An intelligent brain pacemaker can also comprise a seizure detector adapted to detect seizure-related brain activity of a mammal in real-time, the seizure detector being electrically connected to the one or more electrodes. Broadly, this component of the intelligent brain pacemaker performs a real time analysis of incoming field potential data and determines if a seizure is occurring or is predicted to occur. When the seizure detector determines that a seizure is occurring or is predicted to occur, it sends a signal to a nerve stimulator to disrupt or counteract the seizure. The automatic seizure detector operates in real time and does not require manual triggering of a signal or any intervention by a human.

The intelligent brain pacemaker further comprises one or more nerve stimulators adapted to provide electrical stimulation to a mammal's cranial nerve not associated with an autonomic function, to terminate or ameliorate the seizure, the one or more nerve simulators being electrically connected to the seizure detector.

In the fields of neurology and physiology, stimulators are generally employed to generate DC pulses according to a set of operator-specified parameters, which can include pulse amplitude and timing. Relevant timing parameters can include delay, duration, train duration and pulse interval. Delay is the time between single pulses, duration is the length of a single pulse, train duration is the time from the beginning of the first pulse of a train of pulses to the end of the last pulse of the train and pulse interval is the time between the pulses in a train of pulses. Additional parameters that can be controlled by the nerve stimulator include the frequency of the pulses that are delivered. It is preferable to employ a train of pulses in the intelligent brain pacemaker, although discrete pulses can be employed as circumstances dictate and at the discretion of the operator.

When a signal is received from the seizure detection module, the nerve stimulator executes a set of instructions corresponding to the type of nerve stimulation to be provided. The exact nature of an appropriate pulse scheme will be apparent to those of skill in the art upon consideration of the present disclosure, however one pulse scheme that can be employed comprises a 0.5 second pulse train of 500 $\mu$sec pulses delivered at 333 Hz.

Suitable nerve stimulators for practicing the intelligent brain pacemaker include the GRASS Model S8800 stimulator (available from Grass Instruments of Quincy, Mass.). A suitable nerve stimulator will be programmable, thereby allowing a wide range of pulse profiles to be created and delivered.

Additionally, an intelligent brain pacemaker can comprise a power source for providing power to the intelligent brain pacemaker. The power source is preferably adapted to be implanted in or on the body of a patient employing the intelligent brain pacemaker. Although many different types of power sources can be employed in the invention, preferred power sources include lithium batteries.

V.E. Real Time Closed Loop Brain Machine Interface

Through the years there has been significant research in the area of detecting and observing various electric potentials generated within the human body for medical diagnosis, biofeedback control of mental and physical states, and control of external devices. It is known that different regions of the brain are used to control different parts of the body and to process different sensory inputs. It is also known that when a human performs a certain function, such as moving an extremity or listening to a particular sound, multiple regions of the brain generate electrical action potentials to accomplish that function. It is also known that direct electrical stimulation of a particular region of the brain can cause at least partial reproduction of the functions or sensory input normally associated with that region of the brain. Determining which portions of a patient's brain are responsible for certain motor activities or certain sensory functions has become known as brain "mapping." In theory, after a patient's brain has been mapped, the brain can be electrically stimulated to restore lost functions.

For example, it is possible to determine which portions of a patient's brain are responsible for processing signals associated with the movement of an extremity. Once a neurosurgeon knows which portions of the patient's brain are responsible for processing these signals, it is possible to electrically stimulate selected portions of the patient's brain to cause the patient to "move" the extremity. Thus, a patient whose motor control has been partially or permanently damaged can regain motor control if an apparatus is employed to translate these neural signals into movement of an external device, such as an actuator. Similarly, if the areas of the patient's brain that are associated with tactile and other sensory information are known, these areas of the patient's brain can be electrically stimulated to make the patient "experience" the sensory interaction between an object and an external device interacting with the object. The closed loop brain-machine interface employing an array of the present invention makes these and other goals possible and can greatly enhance the quality of life of those individuals whose motor control has been impaired. The microwire electrode arrays of the present invention can form a component of such a real time closed loop brain-machine interface.

The microelectrode arrays 100, 200 of the present invention can form a component of a closed loop brain-machine interface that can translate neural signals in the brain of a subject into movement of an external device adapted to provide sensory feedback to the subject. The microwire electrode arrays of the present invention can be employed in methods and apparatuses for obtaining signals directly from the brain or central nervous system, for processing and utilizing these signals to control one or more external devices, such as an actuator, and for providing a subject with sensory feedback from the external devices.

In a preferred embodiment, a closed loop brain-machine interface comprises a multichannel microwire electrode array for acquiring neural signals from large numbers of single neurons. The array preferably comprises one or more microwire electrodes, as disclosed hereinabove.

The array further comprises one or more printed circuit boards in electrical connection with the one or more microwire electrodes. The PCB(s) preferably comprise one or more conductive traces spaced about 0.015 inches (center to center) or less and one or more conductive pads in electrical connection with the one or more conductive traces. Again, preferred configurations of a PCB are discussed hereinabove.

The array also comprises one or more connectors in electrical connection with the one or more conductive pads and having contacts spaced apart about 0.030 inches (center to center) or less. Preferred connectors can comprise those disclosed hereinabove. Alternatively, a connector can be designed and fabricated based on the preferred connector properties disclosed hereinabove.

Additionally, the closed loop brain-machine interface comprises a signal processing mechanism adapted to communicate with the multichannel microwire electrode array and adapted to form extracted motor commands from the extracellular electrical signals. Processing of brain-derived neural signals can occur, preliminarily, when a data processing unit receives the raw stream of action potentials. Preferably, the majority of signal processing occurs when the gathered neural signals arrive at a processing computer. When the signals arrive at a processing computer, the signals relating to one or more motor command are identified and motor command and/or trajectory data is extracted from the neural signals.

Further, the closed loop brain-machine interface comprises an actuator adapted to communicate with the signal processing mechanism and to respond to the extracted motor commands by effecting a movement, and to provide sensory feedback to the subject. As processed data becomes available, the data (which can comprise impulses to move an actuator to a given three-dimensional coordinate in space) can be broadcasted via TCP/IP-adapted server to one or more computer clients. These clients can be responsible for controlling the 3-D movements of the actuator, such as a robotic arm (e.g., PHANTOM™, available from SensAble Technologies of Woburn, Mass.), or one or more actuators that mimic one or more appendages of a patient.

By employing this approach, one or more remote devices can be controlled directly using brain-derived signals. In this application, as an actuator moves, a signal describing its position in space is recorded on each client machine. Thus, one can measure the accuracy with which both local and remote actuator movements match the trajectory signals generated by one or more models (i.e., a linear model and an ANN model).

Alternatively, as the results from the one or more models become available, they can be broadcasted via telemetry or via a cable or other hardwire link to an actuator. Such an actuator is, therefore, adapted to receive the results.

In another embodiment, a real time closed loop brain-machine interface for restoring voluntary motor control and sensory feedback to a subject that has lost a degree of voluntary motor control and sensory feedback. In a preferred embodiment, the interface comprises a multichannel microwire electrode array for acquiring neural signals from large numbers of single neurons. The array preferably comprises one or more microwire electrodes, as disclosed hereinabove.

The array further comprises one or more printed circuit boards in electrical connection with the one or more microwire electrodes. The PCB(s) preferably comprise one or more conductive traces spaced about 0.015 inches (center to center) or less and one or more conductive pads in electrical connection with the one or more conductive traces. Again, preferred configurations of a PCB are discussed hereinabove.

The array also comprises one or more connectors in electrical connection with the one or more conductive pads and having contacts spaced apart about 0.030 inches (center to center) or less. Preferred connectors can comprise those disclosed hereinabove. Alternatively, a connector can be designed and fabricated based on the preferred connector properties disclosed hereinabove.

The real time closed loop brain-machine interface further comprises an implantable neurochip adapted to communicate with the implantable microwire array and to filter and amplify the one or more neural signals. The one or more implanted neurochips can be fabricated to accomplish a variety of goals. Preferably, a neurochip is adapted to receive the neural signals and to filter and amplify the signals. The precise nature of the signal filtration can vary with the desire of the neurosurgeon implanting a neurochip. Similarly, the degree to which the signals are amplified can vary with the needs of the individual implanting the neurochip or chips. Unique physiological aspects of the patient in whom the neurochip or chips are being implanted can also be taking into account.

An implanted neurochip or collection of neurochips essentially serves as the first stage of the signal processing treatment. After filtering and amplification, the neurochip can multiplex the neural signals and transmit the signals to a data acquisition unit. The mechanism of the transmission can be via a cable or by telemetry of other wireless manner. Preferably, a neurochip is adapted to transmit the signals via telemetry because when this manner of transmission is employed, the skull and scalp of the patient can be fully closed, permitting an implanted neurochip and electrodes to operate without the need for the patient to be physically associated with the data acquisition unit. This approach also minimizes the chances of infection and other undesired conditions.

The real time closed loop brain-machine interface further comprises a motor command extraction microchip adapted to communicate with the implantable neurochip and embodying one or more motor command extraction algorithms, the microchip and the algorithms adapted to extract motor commands from the brain-derived neural signals. When brain-derived motor command signals are received by a processing computer, neural signals relating to motor commands are extracted from the collection of gathered neural signal data. Since a closed loop brain-machine interface that is implanted in a human is preferably in continuous operation following implantation, neural signals will be continuously gathered and relayed to a data processing unit. Many of the gathered neural signals will not be related to motor commands, and therefore, it is desirable to separate signals unrelated to motor commands from signals related to motor commands. Identification algorithms running on a processing computer can perform this identification process. However, identification of signals related to motor commands can be performed at any point before an extraction of motor command or trajectory prediction data is performed. Alternatively, identification of these sequences can be performed as a component of the motor command or trajectory prediction deconvolution. Subsequent to identification of motor command-related signals, a deconvolution is performed to extract a trajectory prediction from the motor command-related signals.

The real time closed loop brain-machine interface further comprises an actuator adapted to communicate with the motor command extraction microchip and to move in response to the motor commands and to acquire sensory feedback information during and subsequent to a movement. As processed data becomes available, the data (which can comprise impulses to move an actuator to a given three-dimensional coordinate in space) can be broadcasted via TCP/IP-adapted server to one or more computer clients. These clients can be responsible for controlling the 3-D movements of the actuator, such as a robotic arm (e.g., PHANTOM™, available from SensAble Technologies of Woburn, Mass.), or one or more actuators that mimic one or more appendages of a patient.

By employing this approach, one or more remote devices can be controlled directly using brain-derived signals. In this application, as an actuator moves, a signal describing its position in space is recorded on each client machine. Thus, one can measure the accuracy with which both local and remote actuator movements match the trajectory signals generated by one or more models (i.e., a linear model and an ANN model).

Alternatively, as the results from the one or more models become available, they can be broadcasted via telemetry or via a cable or other hardwire link to an actuator. Such an actuator is, therefore, adapted to receive the results.

The interface also comprises a sensory feedback microchip embodying one or more sensory feedback information interpretation algorithms adapted to communicate with the actuator, the sensory feedback microchip adapted to form interpreted sensory feedback information.

In operation, sensory feedback, such as size, weight, shape, hardness, temperature or texture, can be acquired when an actuator interacts with a physical object. This interaction can come at the end of a trajectory followed by an actuator, such as when an actuator grasps an object. Alternatively, an interaction can come inadvertently, or by command, as an actuator is following a trajectory deconvoluted from a plurality of brain-derived neural signals.

When an actuator interacts with a physical object, it acquires sensory feedback about the object. This feedback can then be processed by feedback processing circuitry disposed on the actuator itself or at a location remote from the actuator. The processing can be via a microchip adapted to interpret sensory feedback data. The feedback processing circuitry can function to translate tactile information into a signal that can be perceived by a patient. This signal can take the form of a physical stimulation, electrical signals transmitted to the nervous system of a patient or any other form capable of imparting sensory information to a patient.

The interface also comprises a structure adapted to communicate with the sensory feedback microchip and to deliver interpreted sensory feedback information to the subject. For example, a prosthetic limb incorporating a sophisticated controller which permits switching between multiple degrees of freedom and/or multiple functions with myoelectric input from one or more muscle or muscle groups is apparently found in U.S. Pat. No. 5,336,269 issued to Smits. Smits discloses a method and apparatus for switching between a plurality of degrees of freedom, e.g., wrist pronation and supination, elbow flexion and extension, and hand closing and opening. The apparatus comprises at least one surface electrode for picking up myoelectric signals of a muscle, circuitry for amplifying, full-wave rectifying and smoothing the myoelectric signals, an analog-to-digital converter for converting the received myoelectric signals to digital data, and a microcontroller having memory means and programming to operate the apparatus.

Further, the interface comprises one or more power sources adapted to provide power, as necessary, to one or more of the group consisting of the implantable neurochip; the motor command extraction microchip; the actuator; the sensory feedback microchip; and the structure adapted to relay interpreted sensory feedback information to the subject. Preferred power sources comprise lithium batteries.

VII. Advantages of the Present Invention

The microelectrode arrays of the present invention offer many advantages over the prior art. For example, the electrode arrays 100, 200 of the present invention are high-density arrays, they are chronically implantable and they are multichannel arrays, to name just a few advantages over the prior art. These and other advantages of the present invention over the prior art are described hereinbelow.

VII.A. The Electrode Array is a High-Density Array

Prior to the present disclosure, prior art devices could not be employed to acquire large numbers of neural signals from single neurons. This is due, in part, to the limitation that prior art devices could not accommodate more than about 32 microwire electrodes. This number is far less than optimal for neurological research and for a role in clinical applications.

The arrays of the present invention, on the other hand, are high-density arrays and can comprise an unlimited number of microwire electrodes. These arrays facilitate the acquisition of data that is of greater quantity and quality than that obtainable from prior art microwire electrode arrays.

This advance over the prior art can be advantageously applied in various clinical applications, such as the control of epileptic seizures and the treatment of subjects having impaired motor control. Indeed, by virtue of the fact that the arrays of the present invention are high-density arrays, they can form a component of any device adapted to treat a neurological disorder.

The high-density of the arrays of the present invention can also be employed in basic research. Since the arrays of the present invention are high-density arrays, the quantity and quality of data acquired by the arrays can offer further insight into neurological research. For example, since the arrays of the present invention make it possible to acquire a greater volume of data from single neurons, this can offer further insights and can transcend limitations that have inhibited research in the field of neurological research.

VII.B. The Electrode Array is Chronically Implantable

Another advantage of the arrays of the present invention is the ability for these arrays to be chronically implanted in the tissue of a subject. Although it might be possible to implant some prior art arrays in the tissue of a subject, these arrays cannot remain implanted for long periods of time. Some problems associated with these prior art arrays in this regard include degradation of the array itself, irritation of the tissue in which the array is implanted and the large size of the array leads to a risk of damage to the implant itself.

The present invention solves this problem. The arrays 100, 200 of the present invention can easily be implanted and will remain functional for many months and even years. This is due, in part, to the small size of the arrays, which can be crafted on the millimeter scale. Additionally, the arrays of the present invention can be fashioned of materials that are biocompatible and are largely tolerated by the subject. Additionally, the arrays of the present invention can be fashioned from materials that are durable and resistant to the degradation that can attack a device that is implanted in the tissue of a subject.

VIII.C. The Electrode Array is a Multichannel Array

The electrode arrays 100, 200 of the present invention are multichannel arrays. This facilitates acquisition of neural signals from different regions of a subject's neural tissue (e.g. brain) in an isolated fashion. That is, data from a first area can be acquired separately from data acquired from a second area of the subject's neural tissue.

Many prior art devices do not feature this ability. In these devices, all data is acquired on a single channel, which can lead to an overall global average of data, rather than data isolated from single neurons. This global averaging can eliminate or reduce important distinctions between data acquired from different electrodes. Further, those prior art devices that do comprise multiple channels are not adapted to acquire data of the quantity or quality achievable by the arrays of the present invention.

VIII.D. The Electrode Array is Stackable

The electrode arrays 100, 200 of the present invention are stackable. That is, the electrode arrays of the present invention are adapted to be superimposed on one another in a stacked arrangement. An unlimited number of electrode arrays can be stacked together, thereby providing an unlimited number of electrodes for data acquisition.

The modular nature of the arrays of the present invention provides the ability of a researcher or a clinician to design and build an array comprising a desired number of electrodes. For example, some applications might require a lesser number of electrodes, while other applications might require a greater number of electrodes. Both of these types of applications can be accommodated by the arrays of the present invention. To applicants' knowledge, no such array is presently available.

IX. Conclusions

The high-density multichannel microwire electrode arrays 100, 200 of the present invention are an advance over presently available electrode arrays adapted for neurological applications. Specifically, the arrays are of higher density than any other arrays presently available. This is due, in part, to the stackable nature of the arrays. The high-density of the arrays can facilitate acquisition of high quality data in large quantities. This ability is absent from prior art devices.

Additionally, arrays 100, 200 are multichannel arrays, facilitating acquisition of data from different locations (and different electrodes) on different channels. This can be particularly advantageous when the data is processed. For example, data acquired on different channels can be processed differently, with the data on each channel being treated with different algorithms and/or signal treatments.

Further, arrays 100, 200 comprise high-density connectors. Although these elements are known, until the present disclosure, they have not been applied in a high-density multichannel microelectrode array. Indeed, an advantage of the present invention over the art is the ability to employ such high-density connectors. By employing these connectors, it is possible to decrease the overall size of a connector-PCB-electrode assembly, due in part to the high-density of the connector and the overall design of the array.

The stackable nature of arrays 100, 200 of the present invention represents another advance over presently available microwire electrode arrays. The modularity of the arrays allows researchers and clinicians to design and build an array comprising a desired number of electrodes. The ability to tailor an array to a desired size is lacking from prior art devices.

Summarily, the present invention discloses a high-density multichannel microwire electrode array. An array can be employed to acquire neural signals (e.g. electrical signals) from a large number of single neurons. An array can be employed in basic research or as a component of a clinical device, such as an intelligent brain pacemaker or a closed loop brain machine interface, to name just a few devices. Notably, the arrays of the present invention facilitate the acquisition of a larger number of neural signals that previously possible.

REFERENCES

The references listed below as well as all references cited in the specification are incorporated herein by reference to the extent that they supplement, explain, provide a background for or teach methodology, techniques and/or compositions employed herein.

Chicurel, (2001) *Nature*, 412: 266–8
Nicolelis et al., (1997) *Neuron*, 18: 529–37
Nicolelis, (ed.), (1998) *Methods for Neural Ensemble Recordings*, CRC Press, Boca Raton
Paxinos & Watson, (1986) *The Rat Brain*, Ed. 2. New York, Academic, Harcourt, Brace and Jovanovich
U.S. Pat. No. 4,702,254
U.S. Pat. No. 4,867,164
U.S. Pat. No. 5,025,807
U.S. Pat. No. 5,336,269
U.S. Pat. No. 5,540,734
U.S. Pat. No. 6,016,449
U.S. Pat. No. 6,061,593

It will be understood that various details of the invention may be changed without departing from the scope of the invention. Furthermore, the foregoing description is for the purpose of illustration only, and not for the purpose of limitation—the invention being defined by the claims.

What is claimed is:

1. A real time closed loop brain-machine interface comprising:
   (a) a multichannel microwire electrode array for acquiring neural signals from a plurality of single neurons comprising:
      (i) a plurality of microwire electrodes;
      (ii) one or more printed circuit boards in electrical connection with the microwire electrodes comprising:
         (1) a plurality of conductive traces spaced apart about 0.015 inches (center to center) or less; and
         (2) a plurality of conductive pads in electrical connection with the one or more conductive traces; and
      (iii) one or more connectors in communication with conductive pads and having contacts spaced apart about 0.030 inches (center to center) or less;
   (b) a signal processing mechanism adapted to communicate with the multichannel microwire electrode array and adapted to form extracted motor commands from the extracellular electrical signals; and
   (c) an actuator adapted to communicate with the signal processing mechanism and to respond to the extracted motor commands by effecting a movement, and to provide sensory feedback to the subject.

2. The real time closed loop brain-machine interface of claim 1, wherein the microwire electrodes comprise a material selected from the group consisting of stainless steel, tungsten, noble metals, conductive alloys and conductive polymers.

3. The real time closed loop brain-machine interface of claim 1, wherein the microwire electrodes are substantially coated with a material selected from the group consisting of TEFLON®, S-lsonel, polymers, plastics and non-conductive materials.

4. The real time closed loop brain-machine interface of claim 1, wherein the one or more printed circuit boards are flexible and about 0.01 inch thick.

5. The real time closed loop brain-machine interface of claim 1, wherein the one or more printed circuit boards are substantially rigid and about 0.08 inches thick.

6. The real time closed loop brain-machine interface of claim 1, wherein the one or more printed circuit boards comprise a plurality of the circuit boards secured together in a superimposed stacked relationship.

7. The real time closed loop brain-machine interface of claim 1, wherein the one or more printed circuit boards each comprise one or more removable support tabs.

8. The real time closed loop brain-machine interface of claim 1, wherein the conductive traces are substantially insulated.

9. The real time closed loop brain-machine interface of claim 1, wherein the one or more connectors are zero insertion force (ZIF) connectors.

10. The real time closed loop brain-machine interface of claim 1, wherein the one or more connectors are low insertion force (LIF) connectors.

11. The real time closed loop brain-machine interface of claim 1, wherein the one or more connectors comprise a plurality of connectors soldered to the plurality of conductive pads.

* * * * *